(12) United States Patent
Casanova et al.

(10) Patent No.: US 12,186,709 B2
(45) Date of Patent: Jan. 7, 2025

(54) THREE-COMPARTMENT BIPOLAR MEMBRANE ELECTRODIALYSIS OF SALTS OF AMINO ACIDS

(71) Applicant: Monsanto Technology LLC, St. Louis, MO (US)

(72) Inventors: Eduardo Aurelio Casanova, St. Louis, MO (US); Justin Robert Struble, St. Louis, MO (US); Jian Xu, St. Louis, MO (US)

(73) Assignee: Monsanto Technology LLC, Saint Louis, MO (US)

( * ) Notice: Subject to any disclaimer, the term of this patent is extended or adjusted under 35 U.S.C. 154(b) by 684 days.

(21) Appl. No.: 16/972,328

(22) PCT Filed: Jun. 6, 2019

(86) PCT No.: PCT/US2019/035749
§ 371 (c)(1),
(2) Date: Dec. 4, 2020

(87) PCT Pub. No.: WO2019/236814
PCT Pub. Date: Dec. 12, 2019

(65) Prior Publication Data
US 2021/0229040 A1    Jul. 29, 2021

Related U.S. Application Data

(60) Provisional application No. 62/681,205, filed on Jun. 6, 2018.

(51) Int. Cl.
*B01D 61/44* (2006.01)
*B01D 61/46* (2006.01)
(Continued)

(52) U.S. Cl.
CPC .......... *B01D 61/445* (2013.01); *B01D 61/46* (2013.01); *B01D 61/54* (2013.01); *C07C 227/18* (2013.01);
(Continued)

(58) Field of Classification Search
CPC .................... B01D 61/445; B01D 61/465–467
See application file for complete search history.

(56) References Cited

U.S. PATENT DOCUMENTS 3,964,985 A    6/1976   Giuffrida
5,268,079 A    12/1993  Ochoa Gomez et al.
(Continued)

FOREIGN PATENT DOCUMENTS

CN    101234961 A    8/2008
CN    103071389 A    5/2013
(Continued)

OTHER PUBLICATIONS

Bian et al, "Production of Iminodiacetic Acid by Electrodeionization with Bipolar Membrane," (2011) (Year: 2011).*
(Continued)

*Primary Examiner* — Salil Jain
(74) *Attorney, Agent, or Firm* — Harness, Dickey & Pierce, P.L.C.

(57) ABSTRACT

This invention relates to an improved electrodialysis method for preparing an amino acid from a salt of the amino acid utilizing a three-compartment bipolar membrane electrodialysis process wherein an aqueous electrolyte comprising an exogenous acid is added to the acid compartment of a three-compartment bipolar membrane apparatus. The exogenous acid is different than the amino acid and typically has a pKa less than the pKa of the amino acid.

29 Claims, 18 Drawing Sheets

(51) Int. Cl.
    *B01D 61/54*     (2006.01)
    *C07C 227/18*     (2006.01)
    *C07C 227/40*     (2006.01)
    *C07F 9/38*     (2006.01)

(52) U.S. Cl.
    CPC .......... *C07C 227/40* (2013.01); *C07F 9/3813* (2013.01); *B01D 2311/12* (2013.01); *B01D 2311/18* (2013.01)

(56) References Cited

U.S. PATENT DOCUMENTS

| | | | |
|---|---|---|---|
| 6,551,803 | B1 | 4/2003 | Fischer et al. |
| 6,755,951 | B1 | 6/2004 | Mani |

FOREIGN PATENT DOCUMENTS

| | | |
|---|---|---|
| CN | 104119243 A | 10/2014 |
| CN | 104098602 | 8/2016 |
| DE | 19952961 A1 | 5/2001 |
| EP | 0438369 | 7/1991 |
| WO | WO-98/35930 A1 | 8/1998 |
| WO | WO2016/200387 | 12/2016 |

OTHER PUBLICATIONS

Yanfang Bian et al: "Production of iminodiacetic acid by electrodeionization with bipolar membrane" Mechanic Automation and Control Engineering (MACE), 2011 Second Internation Conference On, Jul. 15, 2011, pp. 6694-6697 (4 pages).

Hanna Jaroszek et al: "Ion-exchange membrane in chemical synthesis; a review" Open Chemistry, vol. 14, No. 1, (2015), pp. 1-15 (19 pages).

Qingyou, Zeng et al., "Progress in Synthesis and Separation Technology of Iminodiacetic Acid" Advances In Fine Petrochemicals, vol. 2, No. 10, pp. 23-25. Oct. 2001. (3 pages).

\* cited by examiner

THREE-COMPARTMENT BIPOLAR MEMBRANE ELECTRODIALYSIS OF SALTS OF AMINO ACIDS

CROSS-REFERENCE TO RELATED APPLICATIONS

This application is a U.S. national stage filing under 35 U.S.C. § 371 of International Application No. PCT/US2019/035749, filed on Jun. 6, 2019, which claims the benefit of and priority to U.S. Provisional Application No. 62/681,205, filed on Jun. 6, 2018. The entire disclosure of each of the above applications is incorporated herein by reference.

FIELD OF THE INVENTION

This invention relates to an improved electrodialysis method for preparing an amino acid from a salt of the amino acid utilizing a three-compartment bipolar membrane electrodialysis process wherein an aqueous electrolyte comprising an exogenous acid is added to the acid compartment of a three-compartment bipolar membrane apparatus. The exogenous acid is different than the amino acid and typically has a pKa less than the pKa of the amino acid. The present invention also relates to an electrodialysis method for preparing an amino acid from a salt of the amino acid utilizing a two-compartment bipolar membrane apparatus followed by a three-compartment bipolar membrane apparatus.

BACKGROUND OF THE INVENTION

Bipolar membrane electrodialysis (BME) enables production of an inorganic or organic acid from an inorganic or organic salt, respectively, by water splitting, which provides the protons for the acid formation. Bipolar membranes are capable of splitting water directly into $H^+$ and $OH^-$ ions without the formation of gasses such as $H_2$ or $O^2$. In a bipolar membrane electrodialysis process, the $H^+$ and $OH^-$ ions generated by water splitting in the interfacial region of the membrane migrate under the influence of an electric field to the cathode and anode, respectively. A two-compartment BME cell typically includes a bipolar membrane (BPM) and cation exchange membrane (CEM). For example, typically multiple repeating units of BPM-CEM-BPM are placed between two electrodes thereby forming a two-compartment BME cell containing multiple base and salt compartments. A three-compartment BME cell typically includes a bipolar membrane (BPM), cation exchange membrane (CEM), and anion exchange membrane (AEM). The BPM, CEM, and AEM are placed between two electrodes, forming base, salt, and acid compartments. For purposes of scale, typically multiple repeating units of BPM-CEM-AEM or AEM-CEM-BPM are placed between two electrodes thereby forming a BME cell containing multiple base, salt, and acid compartments to provide multiple product streams. The acid compartment product stream comprises the desired inorganic or organic acid.

Generally, an electrodialysis process requires suitable ion conductivity to achieve a commercially acceptable current efficiency. Acids that dissociate well within the acid compartment are able to maintain sufficient ion conductivity and acceptable current efficiency. Where the acid is unable to achieve the required dissociation, it may be necessary to modify the process. For example, heat may be introduced into the process or a further ion exchange resin may be installed within the acid compartment of the bipolar membrane apparatus.

A need exists in the art for an electrodialysis process utilizing a three-compartment bipolar membrane apparatus and/or a two-compartment bipolar membrane apparatus followed by a three-compartment bipolar membrane apparatus wherein an acid is produced under improved and commercially acceptable current efficiencies that overcomes issues associated with prior methods (e.g., the need to introduce heat into the process or install a further ion exchange resin within the acid compartment of the bipolar membrane apparatus).

SUMMARY OF THE INVENTION

Provided herein is a three-compartment bipolar membrane electrodialysis apparatus and process for improved production of an amino acid from a salt of the amino acid, wherein the process results in commercially acceptable current efficiencies and commercially acceptable yields of amino acid.

The present invention includes three-compartment bipolar membrane electrodialysis processes where the ion conductivity of the acid compartment content is improved by introduction of an aqueous electrolyte comprising an acid different than the amino acid (i.e., an exogeneous acid, also referred to herein as "first acid") into the acid compartment.

Briefly, therefore, the present invention is directed to, a process for preparing an amino acid, the process comprising introducing an aqueous electrolyte comprising a first acid into an acid compartment of a three-compartment electrodialysis bipolar membrane cell comprising an acid compartment, a salt compartment, and a base compartment; introducing a salt stream comprising a salt of the amino acid into the salt compartment of the bipolar membrane cell; and introducing an aqueous stream into the base compartment of the bipolar membrane cell; wherein the first acid and amino acid are different. The present invention is also directed to a process comprising introducing a feed salt stream comprising a salt of the amino acid into the salt compartment of a two-compartment electrodialysis bipolar membrane cell comprising a salt compartment and a base compartment and introducing the product from the salt compartment of the two-compartment electrodialysis bipolar membrane cell as the salt stream for the three-compartment electrodialysis bipolar membrane cell described above.

The present invention is further directed to a process for preparing an amino acid, the process comprising introducing an aqueous electrolyte comprising a first acid into an acid compartment of a three-compartment electrodialysis bipolar membrane cell comprising an acid compartment, a salt compartment, and a base compartment; introducing a salt stream comprising a salt of the amino acid into the salt compartment of the bipolar membrane cell; and introducing an aqueous stream into the base compartment of the bipolar membrane cell, wherein the acid compartment is bounded by a first bipolar membrane and an anionic exchange membrane, wherein the base compartment is bounded by a second bipolar membrane and a cationic exchange membrane, wherein the salt compartment is bounded by the anionic exchange membrane of the acid compartment and the cationic exchange membrane of the base compartment, wherein the process further comprises applying an electric potential between the cathode and the anode, thereby inducing flow of protons in the acid compartment toward the cathode and formation of amino acid anions from the salt of the amino acid in the salt compartment, wherein the amino acid anions pass through the anionic exchange membrane and into the acid compartment; and wherein the first acid and amino acid are different. The present invention is additionally directed to a process comprising introducing a feed salt stream comprising a salt of the amino acid into the salt compartment of a two-compartment electrodialysis bipolar membrane cell comprising a salt compartment and a base compartment and introducing the product from the salt compartment of the two-compartment electrodialysis bipolar membrane cell as the salt stream for the three-compartment electrodialysis bipolar membrane cell described above.

The present invention is also directed to a process for preparing iminodiacetic acid, the process comprising introducing an aqueous electrolyte comprising a first acid into an acid compartment of a three-compartment electrodialysis bipolar membrane cell comprising an acid compartment, a salt compartment, and a base compartment; introducing a salt stream comprising a salt of the amino acid into the salt compartment of the bipolar membrane cell; and introducing an aqueous stream into the base compartment of the bipolar membrane cell. The present invention is additionally directed to a process comprising introducing a feed salt stream comprising a salt of the amino acid into the salt compartment of a two-compartment electrodialysis bipolar membrane cell comprising a salt compartment and a base compartment and introducing the product from the salt compartment of the two-compartment electrodialysis bipolar membrane cell as the salt stream for the three-compartment electrodialysis bipolar membrane cell described above.

The present invention is further directed to a process for recovering an amino acid from an amino acid salt, the process comprising introducing a process stream comprising the amino acid salt into a salt compartment of a three-compartment bipolar membrane apparatus comprising an acid compartment, a salt compartment, and a base compartment, introducing an acid into the acid compartment of the membrane apparatus, wherein the pKa of the acid is less than the pKa of the amino acid. For example, the pKa of the acid is at least about 0.5, at least about 1, at least about 2, or at least about 3 pKa units lower than the pKa of the amino acid. The present invention is additionally directed to a process comprising introducing a feed salt stream comprising a salt of the amino acid into the salt compartment of a two-compartment electrodialysis bipolar membrane cell comprising a salt compartment and a base compartment and introducing the product from the salt compartment of the two-compartment electrodialysis bipolar membrane cell as the amino acid salt for introduction into the salt compartment of the three-compartment bipolar membrane apparatus as described above.

The present invention is still further directed to a process for recovering iminodiacetic acid from an iminodiacetic acid salt, the process comprising introducing a process stream comprising the iminodiacetic acid salt into a salt compartment of a three-compartment bipolar membrane apparatus comprising an acid compartment, a salt compartment, and a base compartment, and introducing an acid into the acid compartment of the membrane apparatus. The present invention is additionally directed to a process comprising introducing a process stream comprising the iminodiacetic acid salt into a salt compartment of a two-compartment electrodialysis bipolar membrane cell comprising a salt compartment and a base compartment and introducing the product from the salt compartment of the two-compartment electrodialysis bipolar membrane cell as process stream comprising the iminodiacetic acid salt for introduction into the salt compartment of the three-compartment bipolar membrane apparatus as described above.

Other objects and features will be in part apparent and in part pointed out hereinafter.

DETAILED DESCRIPTION OF THE INVENTION

Figure 1A:
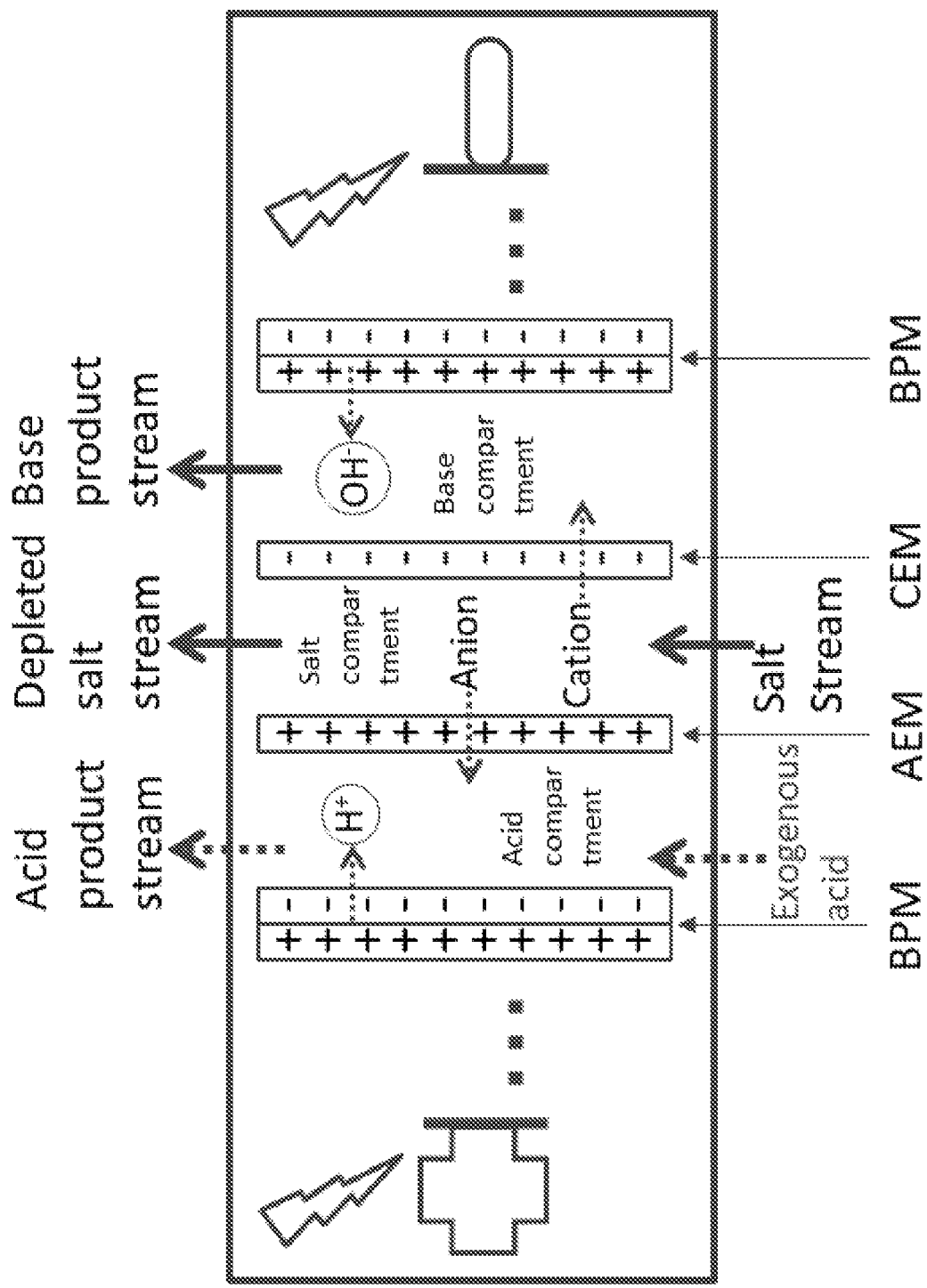
FIG. 1a shows an example configuration of a three-compartment bipolar membrane electrodialysis cell and the flow of the respective ions when subjected to an electric potential between a cathode and anode.

Provided herein are three-compartment bipolar membrane apparatus and processes for producing an amino acid using the three-compartment bipolar membrane apparatus, wherein the feed stream comprises a salt of the amino acid and an aqueous electrolyte comprising an exogenous acid (also referred to herein as "first acid") is introduced into the acid compartment of the bipolar membrane apparatus. As described herein, the feed stream to the salt compartment of the three-compartment bipolar membrane apparatus may be a starting amino acid salt feed stream or may be a salt stream recovered from a salt compartment of a two-compartment bipolar membrane apparatus.

Weak acid production using a three-compartment BME process results in relatively poor current efficiency because of the weak dissociation constant in the acid compartment and corresponding poor ion conductivity. Therefore, bipolar membrane electrodialysis is traditionally only utilized when producing a strong acid. Described herein is an electrodialysis process utilizing a three-compartment bipolar membrane apparatus wherein a weak acid is produced under improved and commercially acceptable current efficiencies that overcomes issues associated with prior methods for producing a weak acid (e.g., the need to introduce heat into the process or install a further ion exchange resin within the acid compartment of the bipolar membrane apparatus). Advantageously, the processes of the present invention provide the amino acid at commercially acceptable yields.

The present invention also relates to a three-compartment bipolar membrane electrodialysis process for preparing an amino acid (e.g., IDA) from a salt of the amino acid (e.g., disodium iminodiacetic acid, i.e., DSIDA) that does not result in the formation of a sodium waste product. For example, the present invention does not result in the formation of a sodium chloride salt waste product when preparing IDA from DSIDA. The present invention relates to preparing an amino acid from a salt of the amino acid, wherein the salt comprises a cation other than sodium. Suitable salt cations may be selected, for example, from the group consisting of potassium, lithium, ammonium, calcium, and magnesium. Further, as detailed below, the present invention also relates to an electrodialysis process utilizing a three-compartment bipolar membrane apparatus and a two-compartment bipolar membrane apparatus for preparing an amino acid from a salt of the amino acid. In accordance with such embodiments, the two-compartment bipolar membrane partially converts the amino acid salt, followed by conversion of the product of the two-compartment apparatus to the desired amino acid. For example, in a process for preparing IDA from DSIDA, the product of the two-compartment bipolar membrane apparatus comprises monosodium iminodiacetic acid (i.e., MSIDA), and the feed stream to the salt compartment of the three-compartment bipolar membrane apparatus comprises MSIDA recovered from the two-compartment BME apparatus.

In various embodiments of the present invention, the three-compartment bipolar membrane apparatus comprises one or more repeating units (i.e., "membrane units") comprising a bipolar membrane (BPM), cation exchange membrane (CEM), and anion exchange membrane (AEM). The one or more repeating membrane units may be selected from, for example, the following configurations: $[BPM\text{-}CEM\text{-}AEM]_n$, $[BPM\text{-}AEM\text{-}CEM]_n$, $[BPM^1\text{-}CEM\text{-}AEM\text{-}BPM^2]_n$, or $[BPM^1\text{-}AEM\text{-}CEM\text{-}BPM^2]_n$, wherein n is the number of repeating units. For example, where the membrane cell comprises one or more repeating membrane unit(s), an anode, and a cathode, generally the bipolar membrane apparatus is characterized by the following configuration: Anode-$\{[BPM\text{-}CEM\text{-}AEM]_n\}$-Cathode or Anode-$\{[BPM\text{-}AEM\text{-}CEM]_n\}$-Cathode. Non-limiting examples of this can be seen in FIGS. 1a, 1b, 2a, and 2b. For example, the bipolar membrane apparatus may comprise the following configuration of repeating membrane units: $[BPM\text{-}CEM\text{-}AEM]_n$ wherein n can be any whole number. For example, n may be 10, 20, 30, 40, 50, 60, 70, 80, 90, 100, 110, 120, 130, 140, 150, 170, 190, 210, 230, 250, 270, 290, or 300. In certain preferred embodiments, n is 7. In other preferred embodiments, n is a whole number from about 1 to about 300 or from about 1 to about 200.

Generally, along with the membrane cell, anode, and cathode the three-compartment bipolar membrane apparatus of the present invention may include one or more terminal or end membranes positioned between the one or more repeating membrane units and the anode and/or between the one or more repeating membrane units and the cathode. The terminal or end membrane(s) may be an AEM, CEM, or BPM.

In certain embodiments, the three-compartment bipolar membrane apparatus comprises a membrane cell comprising one or more repeating membrane unit(s), an anode, and a cathode and, generally is characterized by the following configuration: Anode-$\{CEM[BPM\text{-}AEM\text{-}CEM]_nCEM\}$-Cathode wherein the number of repeating membrane units "n" can be any whole number as described above. In further embodiments, the bipolar membrane apparatus comprises a membrane cell comprising one or more repeating membrane unit(s), an anode, and cathode and has the following configuration: Anode-$\{AEM[AEM\text{-}CEM\text{-}BPM]_nAEM\}$-Cathode. For example, n can be any whole number from 1 to 100, such as 2, 5, 7, 10, 12, 15, or 20.

Figure 1B:
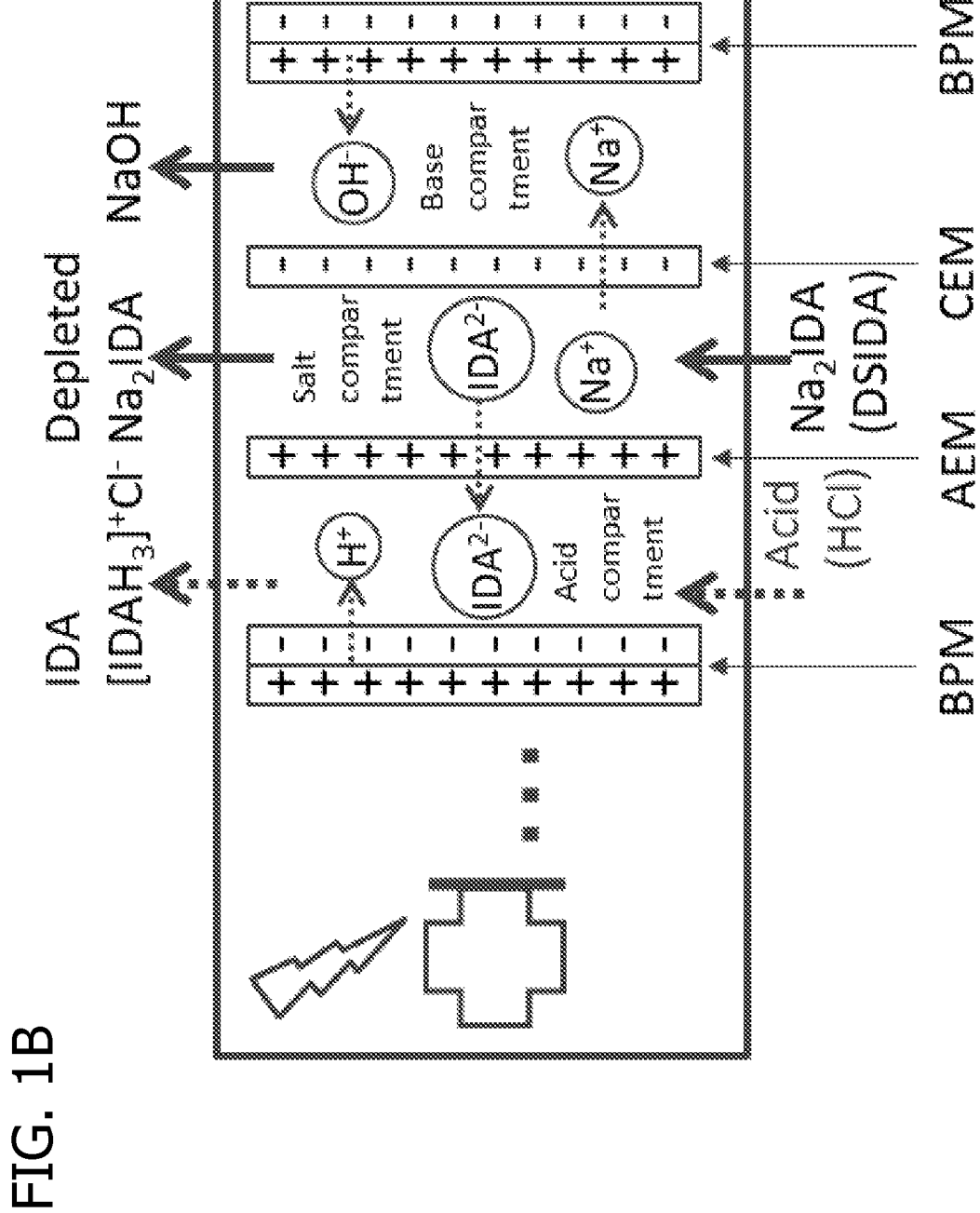
FIG. 1b shows the same configuration as FIG. 1a with a feed stream comprising DSIDA and an exogenous acid comprising HCl.

In other embodiments, the three-compartment membrane cell, comprising one or more repeating membrane units, begins with a bipolar membrane and terminates with a bipolar membrane. For example, the membrane cell may comprise one or more repeating [BPM-CEM-AEM] membrane units and be of the following configuration: Anode-$\{[BPM^1\text{-}CEM\text{-}AEM]_nBPM^2\}$-Cathode, wherein n can be any whole number from 1 to 200. For example, the membrane cell may be of the configuration: $BPM^1\text{-}CEM\text{-}AEM\text{-}BPM^2$ as shown in FIGS. 1a and 1b. In another embodiment the membrane cell may comprise one or more repeating [BPM-AEM-CEM] membrane units and be of the following configuration: Anode-$\{[BPM^1\text{-}AEM\text{-}CEM]_nBPM^2\}$-Cathode, wherein n can be any whole number from 1 to 200.

Alternatively, the three-compartment membrane cell comprising one or more repeating membrane units may begin with a cationic exchange membrane and terminate with a cationic exchange membrane. For example, Anode-$\{CEM[BPM\text{-}AEM\text{-}CEM]_n\}$-Cathode or Anode-$\{[CEM$-

BPM-AEM]$_n$CEM}-Cathode. In another embodiment, the membrane cell comprising one or more repeating membrane units, may begin with an anionic exchange membrane and terminate with an anionic exchange membrane. For example, Anode-{[AEM-CEM-BPM]$_n$AEM}-Cathode or Anode-{AEM[BPM-CEM-AEM]$_n$}-Cathode.

By utilizing one of the above mentioned configurations, the three-compartment membrane cell forms one or more distinct acid, salt (feed), and base compartments. For example, in the embodiment of FIG. 1a, the acid compartment is bounded by the first bipolar membrane and an anionic exchange membrane, the base compartment is bounded by a second bipolar membrane and a cationic exchange membrane, and the salt compartment is bounded by the anionic exchange membrane of the acid compartment and the cationic exchange membrane of the base compartment. Embodiments wherein the membrane cell comprises one or more repeating membrane units and is configured such that the one or more repeating membrane units terminates on each end with a bipolar membrane allows for water splitting to occur at a location immediately adjacent to each acid and base compartment. Embodiments wherein the membrane cell comprises one or more repeating membrane units and is configured such that the one or more repeating membrane units terminates on each end with a cation exchange membrane allows for the introduction of a basic solution adjacent to the cathode and anode. Embodiments wherein the membrane cell comprises one or more repeating membrane units and is configured such that the one or more repeating membrane units terminates on each end with a anionic exchange membrane allows for the introduction of an acidic solution adjacent to the cathode and anode.

Figure 2A:
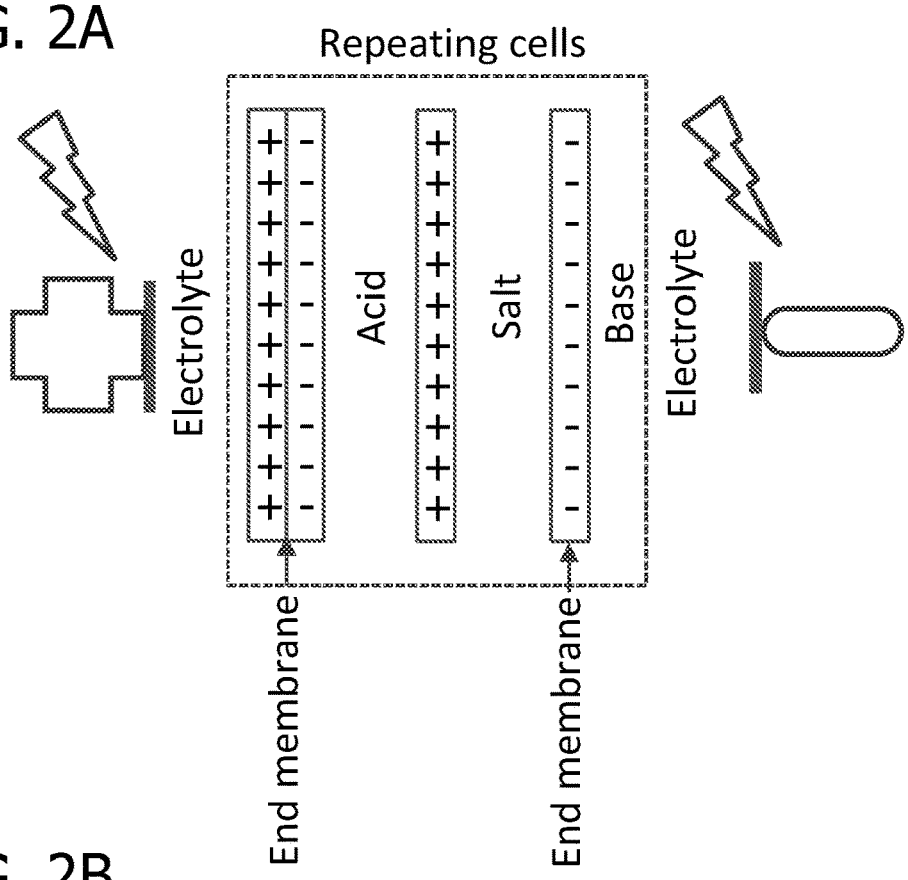
FIG. 2a shows a typical repeating cell for a three-compartment bipolar membrane electrodialysis assembly.
Figure 2B:
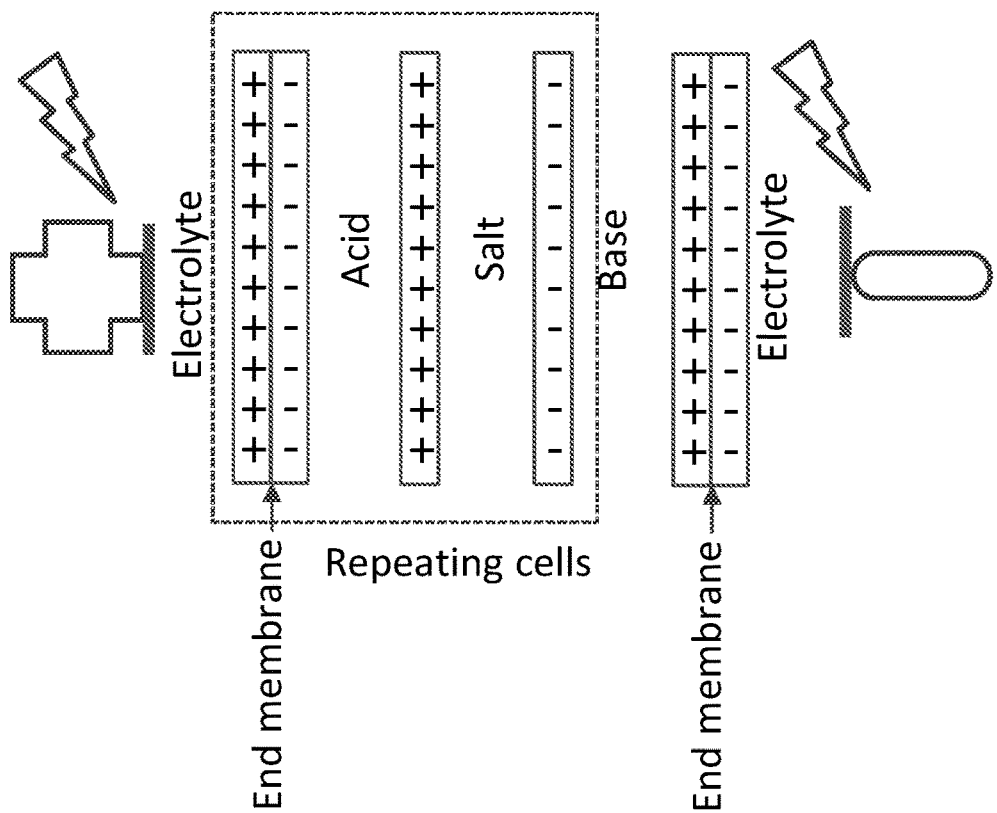
FIG. 2b shows an alternative three-compartment bipolar membrane electrodialysis cell assembly wherein the end membranes are bipolar membranes.

FIG. 2a shows a three-compartment bipolar membrane electrodialysis cell—Anode{[BPM-AEM-CEM]$_n$}Cathode—wherein the repeating membrane units are of the [BPM-AEM-CEM] configuration. FIG. 2b shows an alternative three-compartment bipolar membrane electrodialysis cell—Anode{[BPM-AEM-CEM]$_n$BPM}Cathode—wherein the repeating membrane units are of the [BPM-AEM-CEM] configuration and the membrane cell comprising one or more repeating membrane units terminates on each end with a bipolar membrane.

Figure 2C:
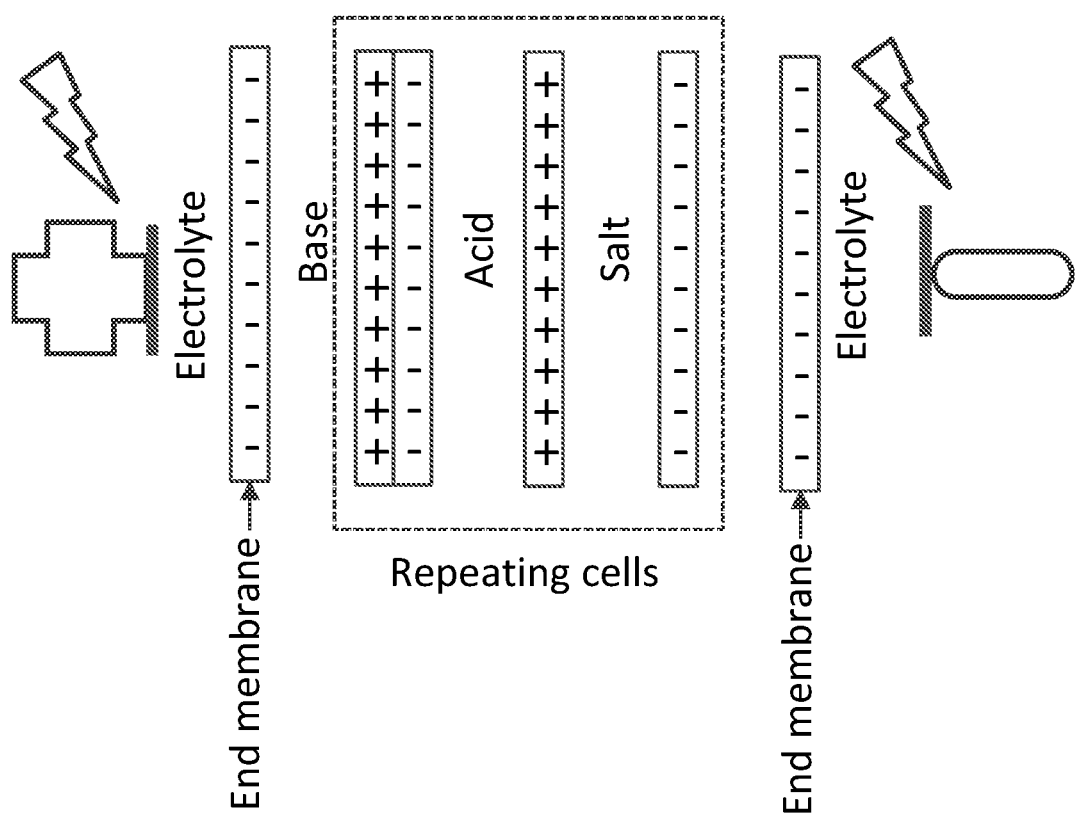
FIG. 2c shows an alternative three-compartment bipolar membrane electrodialysis cell assembly wherein the end membranes are cation exchange membranes.

FIG. 2c shows another alternative three-compartment bipolar membrane electrodialysis cell—Anode{CEM[BPM-AEM-CEM]$_n$CEM}Cathode—wherein the repeating membrane units are of the [BPM-AEM-CEM] configuration and the membrane cell comprising one or more repeating membrane units terminates on each end with a cationic exchange membrane. Although shown as cationic exchange membranes in FIG. 2c, the terminal or end membranes may also be anionic exchange membranes and/or bipolar membranes.

In the bipolar membrane electrodialysis process of the present invention, the three-compartment bipolar membrane cell comprising one or more repeating membrane unit(s) is located between a cathode at one end and an anode at the other end. An electric potential is applied between the cathode and anode, thereby inducing flow of protons in the acid compartment toward the cathode and formation of amino acid anions from the salt of the amino acid in the salt compartment, wherein the amino acid anions pass through the anionic exchange membrane and into the acid compartment. The electric potential also induces flow of hydroxide ions toward the anode and formation of amino acid cations from the salt of the amino acid in the salt compartment, wherein the amino acid cations pass through the cationic exchange membrane and into the base compartment. The anions from the salt of the amino acid and the protons combine in the acid compartment to form the amino acid. The cations from the salt of the amino acid and the hydroxide ions combine in the base compartment to form a base. FIG. 1a shows an example of the configuration of a membrane cell comprising a single BPM[1]-AEM-CEM-BPM[2] membrane unit and the flow of the respective ions when subjected to an electric potential between a cathode and anode. FIG. 1b shows the ion flow for a BPM[1]-AEM-CEM-BPM[2] membrane unit wherein the feed comprises DSIDA and the exogenous acid comprises HCl.

Amino Acid

Although reference is made herein to the amino acid iminodiacetic acid (IDA) and the amino acid salt disodium iminodiacetic acid (DSIDA), it understood that the apparatuses and processes described herein are applicable to numerous other amino acids and their salts.

The amino acid IDA is an essential component in the production of glyphosate (i.e. N-(phosphonomethyl)glycine). However, conventional methods for the production of IDA typically result in the formation of a sodium chloride salt as a waste product. The further processing of this waste product for proper disposal requires considerable cost and effort. Therefore, it is desirable to produce IDA through a process that does not result in formation of a sodium chloride salt waste product.

In various embodiments of the invention, the amino acid has the following structure:

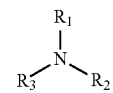

wherein $R_1$ is selected from the group consisting of $CH_2C(O)OH$, $CH_2P(O)(OH)_2$, and hydrogen; $R_2$ is selected from the group consisting of $CH_2C(O)OH$, $CH_2P(O)(OH)_2$, and hydrogen; and $R_3$ is selected from the group consisting of $CH_2C(O)OH$, $CH_2P(O)(OH)_2$, and hydrogen. In a preferred embodiment, $R_1$, $R_2$, and $R_3$ are independently selected from the group consisting of $CH_2C(O)OH$, $CH_2P(O)(OH)_2$, and hydrogen.

In further embodiments the amino acid is selected from the group consisting of iminodiacetic acid (including disodium iminodiacetic acid and monosodium iminodiacetic acid), N-(phosphonomethyl)iminodiacetic acid, glycine, and N-(phosphonomethyl)glycine. As described elsewhere herein, a process combining use of a two-compartment bipolar membrane and three-compartment bipolar membrane apparatus can be used to prepare IDA from DSIDA. In such a process, the two-compartment bipolar membrane apparatus converts DSIDA to MSIDA, with MSIDA being the amino acid salt fed to the three-compartment bipolar membrane apparatus.

In further embodiments the amino acid is selected from the group consisting of alanine, serine, threonine, cysteine, valine, leucine, isoleucine, methionine, proline, phenylalanine, tyrosine, tryptophan, asparitic acid, glutamic acid, asparagine, glutamine, histidine, lysine, and arginine, and salts thereof. Suitable salt cations may be selected, for example, from the group consisting of potassium, lithium, ammonium, calcium, and magnesium.

In certain preferred embodiments, the amino acid is iminodiacetic acid.

Addition of Exogenous Acid into Acid Compartment of the Three-Compartment Bipolar Membrane Apparatus One aspect of the present invention is the introduction of an aqueous electrolyte comprising an exogenous acid (i.e., "first acid") into the acid compartment of the three-compartment bipolar membrane apparatus set forth above. This is illustrated, for example, in FIGS. 1a and 1b. It has been reported in the art that attempts at producing a weak acid using a three-compartment BME process result in relatively poor current efficiency because of the weak dissociation constant in the acid compartment and corresponding poor ion conductivity.

It has been discovered that the addition of an aqueous electrolyte comprising an exogenous acid into the acid compartment, as shown for example in FIGS. 1a and 1b, results in a considerable increase in solubility of the amino acid, and therefore the conductivity of the content of the acid compartment. The acid-base behavior of the amino acid (e.g., IDA) allows for the conductivity of the contents of the acid compartment to increase when an exogenous acid is added and results in the remainder of the acid (e.g., IDA) being maintained in solubilized form. Consequently a greater amount of the salt (e.g., DSIDA) anions pass through the anionic exchange membrane into the acid compartment to combine with the protons from the water-splitting and form the desired acid (e.g., IDA).

It is preferred that the exogenous acid has a pKa lower than the pKa of the salt of the amino acid introduced into the salt compartment. For example, the pKa of the exogenous acid is at least about 0.5, at least about 1, at least about 2, at least about 3, or at least about 4 pKa units lower than the pKa of the salt of the amino acid introduced into the salt compartment. In certain embodiments, the salt of the amino acid has a pKa greater than about 2.0, greater than about 3.0, or greater than about 4.0 and the exogenous acid has a pKa less than the pKa of the salt of the amino acid.

In other embodiments, it is preferred that the exogenous acid has a pKa lower than the pKa of the amino acid produced by the process. For example, the pKa of the exogenous acid is at least about 0.5, at least about 1, at least about 2, or at least about 3 pKa units lower than the pKa of the amino acid. In certain embodiments, the amino acid has a pKa greater than about 1.5, greater than about 2.0, greater than about 2.5, or greater than about 3.0 and the exogenous acid has a pKa less than the pKa of the amino acid produced by the process.

Figure 3:
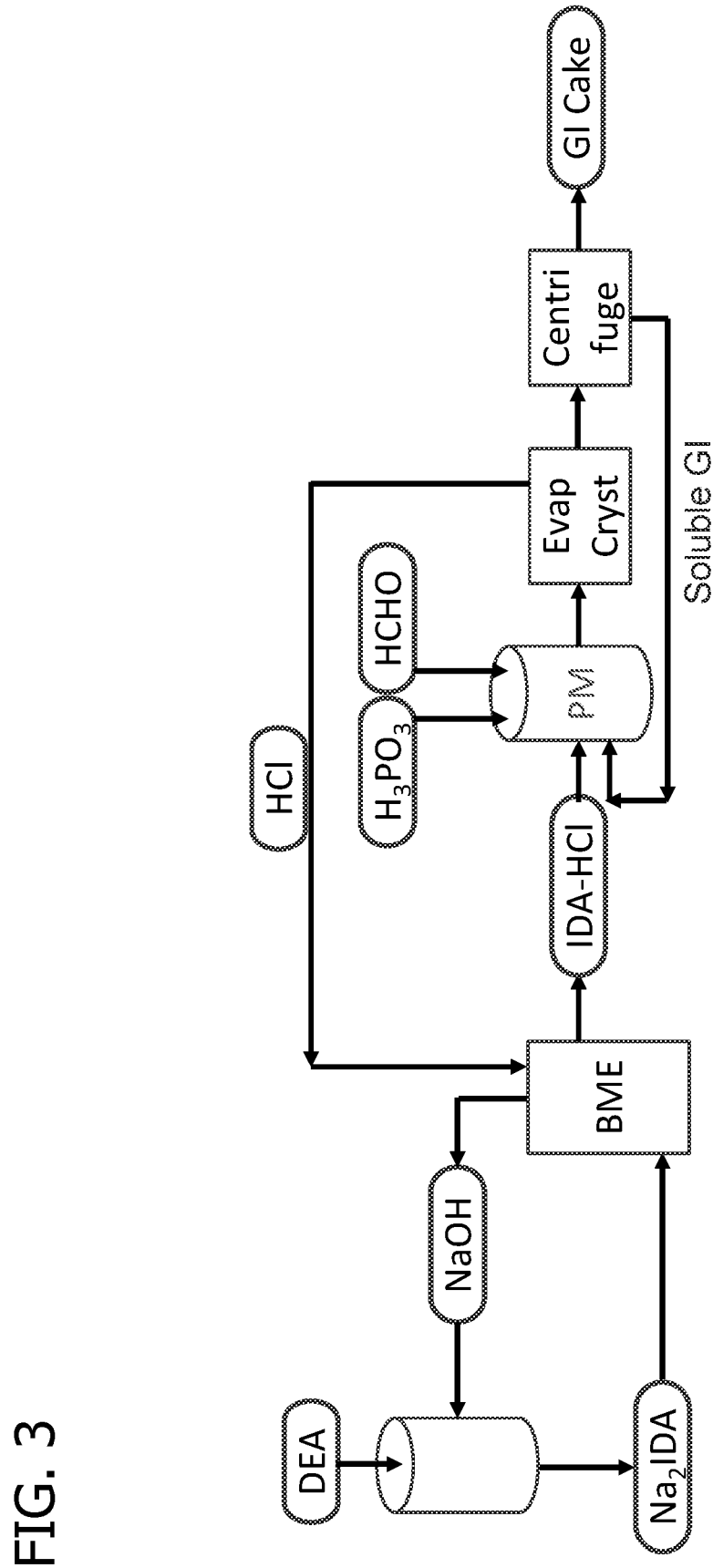
FIG. 3 shows the bipolar membrane electrodialysis (BME) process in the context of an N-(phosphonomethyl)iminodiacetic acid (PMIDA) production operation.

In certain embodiments, a portion of the base group ($-NH_2$) of the IDA amino acid can collect a proton from the aqueous electrolyte comprising an exogenous acid (e.g., HCl) and form a $[IDAH_3]^+$ $Cl^-$ salt within the acid compartment. Depending on the pH of the acid compartment, IDA, $[IDAH_3]^+$ $Cl^-$, or a mixture of both may be recovered in the product stream from the acid compartment. Preferably, the pH is below 2. More preferably, the pH is below 1. As one skilled in the art understands that the pH is dependent on the target concentration of IDA, an increased IDA concentration typically results in a lower pH. As a result of the presence of $[IDAH_3]^+$ $Cl^-$ within the acid compartment, ion conductivity within the compartment increases. Additionally, an increase in current efficiency as compared to a process where exogenous acid is not introduced into the acid compartment is observed. Any $[IDAH_3]^+$ $Cl^-$ salt produced in the acid compartment by addition of the exogenous HCl can be sent to a phosphonomethylation reactor ("PM") and concentrated by evaporation (as shown in FIG. 3), which eliminates the need for crystallization and reslurry. In the phosphonomethylation reactor, HCl is released from $[IDAH_3]^+$ $Cl^-$ salt when glyphosate is formed and precipitates out from the solution. This HCl can then be sent back to the acid compartment of the three-compartment bipolar membrane electrodialysis apparatus in order to reduce the total cost and amount of acid added to the acid compartment by the aqueous electrolyte. FIG. 3 shows an example of a process flow diagram of this three-compartment BME process in the context of preparation of N-(phosphonomethyl) iminodiacetic (PMIDA) that may be involved in a glyphosate production operation. The "BME" component of the flow diagram may be a three-compartment bipolar membrane electrodialysis apparatus or a two-compartment bipolar membrane electrodialysis apparatus followed by a three-compartment bipolar membrane electrodialysis apparatus.

In certain embodiments, the aqueous electrolyte introduced into the acid compartment of the three-compartment bipolar membrane electrodialysis apparatus comprises an acid selected from the group consisting of HCl, $H_2SO_4$, $HNO_3$, $H_3PO_4$, HI, and combinations thereof. In a preferred embodiment, the aqueous electrolyte comprises hydrochloric acid.

In certain embodiments, the molar ratio of the salt of the amino acid introduced into the salt compartment to the acid of the aqueous electrolyte introduced into the acid compartment is at least about 1:0.5, at least about 1:0.75, at least about 1:1, at least about 1:1.1, at least about 1:1.2, at least about 1:1.3, at least about 1:1.4, at least about 1:1.5, at least about 1:2, at least about 1:4, at least about 1:6, at least about 1:8, at least about 1:10, at least about 1:15, or at least about 1:20. For example, in certain embodiments the molar ratio of the salt of the amino acid introduced into the salt compartment to the acid of the aqueous electrolyte introduced into the acid compartment is from about 1:0.75 to about 1:20, from about 1:1 to about 1:10, from about 1:1 to about 1:6, from about 1:1 to about 1:4, from about 1:1 to about 1:2, from about 1:1 to about 1:1.5, from about 1:1.1 to about 1:1.4, or from about 1:1.1 to about 1:1.3.

In certain embodiments, the temperature of the aqueous electrolyte comprising an acid introduced into the acid compartment of the three-compartment bipolar membrane electrodialysis apparatus is from about 10° C. to about 45° C., from about 15° C. to about 40° C., from about 15° C. to about 35° C., or from about 20° C. to about 30° C. when introduced into the acid compartment. For example, the temperature of the aqueous electrolyte comprising an acid introduced into the acid compartment of the three-compartment bipolar membrane electrodialysis apparatus may be about 15° C., about 20° C., about 22° C., about 24° C., or about 25° C. when introduced into the acid compartment.

Three-Compartment Bipolar Membrane Apparatus

Acid Compartment

As set forth above, an aqueous electrolyte comprising an exogenous acid is introduced into the acid compartment of the three-compartment bipolar membrane apparatus. The addition of this aqueous electrolyte results in an increased ion conductivity of the content of the acid compartment. Consequently a greater amount of the anions of the salt of the amino acid pass through the anionic exchange membrane and into the acid compartment. The anions from the salt of the amino acid and the protons from the water splitting process of the bipolar membrane combine in the acid compartment to form the amino acid. FIGS. 1a, 1b, 2a, and 2b illustrate different configurations for the introduction of exogenous acid into the acid compartment. FIGS. 1a and 1b additionally show examples of the flow of ions during the process.

The contents of the acid compartment may comprise the aqueous electrolyte, anions of the salt of the amino acid, ions from the water-splitting operation of the bipolar membrane, water, or any combination thereof.

In certain embodiments the aqueous electrolyte is introduced into the acid compartment gradually such that the pH within the acid compartment does not vary by more than about 1 pH units per minute, more than about 2 pH units per minute, or more than or about 3 pH units per minute.

In another embodiment the pH of the contents of the acid compartment is less than about 3.0, less than about 2.5, less than about 2.0, less than about 1.5, less than about 1.0, less than about 0.9, less than about 0.8, or less than about 0.7.

In yet another embodiment, the conductivity of the content of the acid compartment is at least about 20 mS/cm, at least about 30 mS/cm, at least about 40 mS/cm, or at least about 50 mS/cm. For example, in certain embodiments, the conductivity of the contents within the acid compartment is from about 20 mS/cm to about 300 mS/cm, from about 20 mS to about 200 mS/cm, from about 20 to about 100 mS/cm, or from about 20 mS/cm to about 50 mS/cm.

In certain embodiments, the process further comprises recovering an acid product stream comprising the amino acid from the acid compartment. For example, in certain embodiments, the amino acid constitutes at least about 2 wt %, at least about 4 wt %, at least about 6 wt %, at least about 8 wt %, at least about 10 wt %, at least about 12 wt %, at least about 14 wt %, at least about 16 wt %, at least about 18 wt %, or at least about 20 wt % of the acid product stream. In another embodiment, the amino acid constitutes from about 2 to about 20 wt %, from about 4 wt % to about 18 wt %, from about 6 wt % to about 16 wt %, from about 6 wt % to about 14 wt %, from about 8 wt % to about 14 wt %, or from about 8 wt % to about 12 wt % of the acid product stream. In certain embodiments, the acid product stream further comprises a salt of the amino acid.

In certain embodiments, the amino acid content of the acid product stream represents a yield based on the amino acid salt introduced into the salt compartment $$\left(e.g., \frac{\text{moles iminodiacetic acid recovered from acid compartment}}{\text{moles iminodiacetic acid}^{-2} \text{ in } DSIDA \text{ feed}} \times 100\right).$$

For example, the yield may be at least about 60%, at least about 70%, at least about 80%, at least about 90%, at least about 91%, at least about 92%, at least about 93%, at least about 94%, at least about 95%, at least about 96%, at least about 97%, at least about 98%, or at least about 99%. For example, in certain embodiments, at least about 80% of the salt of the amino acid introduced into the salt compartment is converted to the amino acid recovered in the amino acid product stream. In a preferred embodiment, the target yield of amino acid is at least about 80%, at least about 85%, at east about 90%, or at least about 95%.

Although the pH, conductivity, amino acid content of the product stream, and the amino acid yield are discussed with respect to a three-compartment bipolar membrane electrodialysis apparatus, it is understood that these values correspond to either a three-compartment bipolar membrane electrodialysis process or a process comprising a two-compartment bipolar membrane electrodialysis apparatus followed by a three-compartment bipolar membrane electrodialysis apparatus, as discussed in further detail below.

Salt Compartment

A feed salt stream comprising a salt of the amino acid is introduced into the salt compartment of the three-compartment bipolar membrane apparatus. The electric potential of the electrodialysis process induces formation of amino acid anions from the salt of the amino acid in the salt compartment and transport of the amino acid anions through the anionic exchange membrane and into the acid compartment. Likewise, the electric potential induces formation of amino acid cations from the salt of the amino acid in the salt compartment and transport of the amino acid cations through the cationic exchange membrane and into the base compartment. An example of this transport of cations and anions from the inlet salt stream comprising a salt of an amino acid can be seen in FIGS. 1a and 1b. In a preferred embodiment, the stream exiting the salt compartment is substantially depleted in content of the salt of the amino acid.

In certain embodiments, the concentration of salt of the amino acid in the feed salt stream may be at least about 5 wt %, at least about 10 wt %, at least about 20 wt %, at least about 30 wt %, or at least about 40 wt %. For example, the concentration of salt of the amino acid in the feed salt stream may be from about 5 wt % to about 60 wt %, from about 10 wt % to about 50 wt %, from about 15 wt % to about 50 wt %, from about 20 wt % to about 50 wt %, from about 25 wt % to about 50 wt %, from about 30 wt % to about 50 wt %, from about 35 wt % to about 50 wt %, from about 40 wt % to about 50 wt %, or from about 40 wt % to about 45 wt %.

The contents of the salt compartment after introduction of the feed salt stream, in addition to the salt of the amino acid, may comprise amino acid anions, amino acid cations, ions from the water-splitting operation of the bipolar membrane, water, or any combination thereof.

In certain embodiments, the concentration of salt of the amino acid in the salt compartment may be at least about 1 wt %, at least about 5 wt %, at least about 10 wt %, at least about 15 wt %, at least about 20 wt %, at least about 25 wt %, at least about 30 wt %, at least about 35 wt %, at least about 40 wt %, or at least about 45 wt %. For example, the concentration of salt of the amino acid in the salt compartment may be from about 5 wt % to about 45 wt %, from about 10 wt % to about 35 wt %, from about 10 wt % to about 30 wt %, from about 15 wt % to about 30 wt %, or from about 20 wt % to about 30 wt %.

In certain embodiments, the conductivity of the salt stream introduced into the salt compartment is at least about 10 mS/cm, at least about 20 mS/cm, at least about 25 mS/cm, at least about 50 mS/cm, at least about 100 mS/cm, at least about 150 mS/cm, at least about 200 mS/cm, or at least about 250 mS/cm. In another embodiment, the conductivity of the salt stream introduced into the salt compartment is between about 10 and about 250 mS/cm, between about 20 and about 200 mS/cm, between 25 and about 200 mS/cm, between about 50 and about 200 mS/cm, between about 100 and about 200 mS/cm, or between about 150 and about 200 mS/cm.

In another embodiment, the conductivity of the content of the salt compartment is less than about 200 mS/cm, less than about 100 mS/cm, less than about 75 mS/cm, or less than about 50 mS/cm. For example, in certain embodiments, the conductivity of the content of the salt compartment is from about 200 mS/cm to about 0 mS/cm, from about 100 mS to about 0 mS/cm, from about 75 to about 0 mS/cm, or from about 50 mS/cm to about 0 mS/cm.

In another embodiment, the process further comprises recovering a depleted salt stream from the salt compartment. In certain embodiments, the depleted salt stream comprising less than about 5 wt %, less than about 4 wt %, less than about 3 wt %, less than about 2 wt %, less than about 1 wt %, or less than about 0.5 wt % of the salt of the amino acid.

In certain embodiments, the pH of the salt compartment is at least about 8, at least about 9, at least about 9.5, at least about 10, at least about 10.5, at least about 11, at least about 11.5, or at least about 12.

Although the salt compartment concentration, conductivity, pH, and depleted salt stream are discussed with respect to a three-compartment bipolar membrane electrodialysis apparatus, it is understood that these values correspond to either a three-compartment bipolar membrane electrodialysis process or a process comprising a two-compartment bipolar membrane electrodialysis apparatus followed by a three-compartment bipolar membrane electrodialysis apparatus, as discussed in further detail below.

Base Compartment

As set forth above, the electric potential of the electrodialysis process induces flow of hydroxide ions toward the anode and formation of amino acid cations from the salt of the amino acid in the salt compartment, wherein the amino acid cations pass through the cationic exchange membrane and into the base compartment of the three-compartment bipolar membrane apparatus. The cations from the salt of the amino acid and hydroxide ions combine in the base compartment to form a base. This can be seen, for example, in FIGS. 1a and 1b.

The contents of the base compartment may comprise cations of the salt of the amino acid, ions from the water-splitting operation of the bipolar membrane, water, or any combination thereof.

In certain embodiments, the conductivity of the content of the base compartment is at least about 10 mS/cm, at least about 20 mS/cm, at least about 50 mS/cm, at least about 100 mS/cm, at least about 150 mS/cm, or at least about 200 mS/cm. For example, in certain embodiments, the conductivity of the content of the base compartment is from about 10 mS/cm to about 500 mS/cm, from about 10 mS to about 250 mS/cm, from about 50 to about 250 mS/cm, from about 100 to about 250 mS/cm, from about 150 to about 250 mS/cm, or from about 200 mS/cm to about 250 mS/cm.

In yet a further embodiment, the process further comprises recovering a base product stream from the base compartment. In certain embodiments, the base content of the base product stream represents a yield based on the cation of the amino acid salt (e.g., (moles NaOH recovered from base compartment)/(moles $Na^+$ in DSIDA feed)×100) of at least about 90%, at least about 91%, at least about 92%, at least about 93%, at least about 94%, at least about 95%, at least about 96%, at least about 97%, at least about 98%, or at least about 99%.

Although the base compartment conductivity, base product stream, and yield are discussed with respect to a three-compartment bipolar membrane electrodialysis apparatus, it is understood that these values correspond to either a three-compartment bipolar membrane electrodialysis process or a process comprising a two-compartment bipolar membrane electrodialysis apparatus followed by a three-compartment bipolar membrane electrodialysis apparatus, as discussed in further detail below.

Membranes

Suitable cationic exchange membranes are commercially available from manufacturers such as Suez Water Technologies, Astom (e.g., NEOSEPTA), Fumatech, Allied Corporation, Tokuyama Soda, and WSI Technologies.

Suitable anionic exchange membranes are commercially available from manufacturers such as Suez Water Technologies, Astom (e.g., NEOSEPTA), Fumatech, Allied Corporation, Tokuyama Soda, and WSI Technologies.

Suitable bipolar membranes are commercially available from manufacturers such as Suez Water Technologies, Astom (e.g., NEOSEPTA), Fumatech, Allied Corporation, Tokuyama Soda, and WSI Technologies.

Power Usage and Efficiency

In certain embodiments, applying an electric potential between the cathode and the anode of the three-compartment electrodialysis bipolar membrane or the two-compartment electrodialysis bipolar membrane and three-compartment electrodialysis bipolar membrane comprises application of at least about 1 A (amps), at least about 5 A, at least about 8 A, at least about 10 A, or at least about 13 A.

In another embodiment, applying an electric potential between the cathode and the anode of the three-compartment electrodialysis bipolar membrane or the two-compartment electrodialysis bipolar membrane and three-compartment electrodialysis bipolar membrane comprises application of at least about 5 V (volts), at least about 8 V, at least about 13 V, at least about 15 V, at least about 20 V, at least about 25 V, or at least about 23 V.

In certain embodiments, the current efficiency based on the transport of the cation of the salt of the amino acid to the base compartment of the three-compartment electrodialysis bipolar membrane or transport of the cation of the salt of the amino acid to the base compartment of both the two-compartment electrodialysis bipolar membrane and three-compartment electrodialysis bipolar membrane. The current efficiency can be calculated using the following formula:

$$\frac{\text{Moles of } Na^+ \text{ converted}}{\text{Moles of electrons provided}}$$

wherein the moles of electrons provided is determined by the formula:

$$(\text{total number of repeating membrane units}) \times \frac{I \cdot t}{F}.$$

I is the current intensity reported in units of amps or coulombs, F is the faraday constant (96,485 C $mol^{-1}$), and t represents time.

For example, the current efficiency is at least about 85%, at least about 87%, at least about 89%, at least about 91%, at least about 93%, at least about 95%, at least about 96%, at least about 97%, at least about 98%, or at least about 99%. For example, in certain embodiments, the current efficiency based on the transport of the cation of the salt of the amino acid to the base compartment is from about 85% to about 99%, from about 89% to about 99%, or from about 95% to about 99%.

In another embodiment, the current efficiency based on the transport of the anion of the salt of the amino acid to the acid compartment of the three-compartment electrodialysis bipolar membrane is at least about 75%, at least about 76%, at least about 77%, at least about 78%, at least about 79%, at least about 80%, at least about 82%, at least about 84%, at least about 86%, at least about 88%, at least about 90%, at least about 95%, or at least about 99%. For example, in certain embodiments, the current efficiency based on the transport of the anion of the salt of the amino acid to the acid compartment is from about 75% to about 99%, from about 80% to about 99%, or from about 90% to about 99%.

In certain embodiments, the power usage is less than about 5 kW/hr, less than about 4 kW/hr, less than about 3 kW/hr, less than about 2 kW/hr, less than about 1 kW/hr, less than about 0.75 kW/hr, less than about 0.7 kW/hr, less than about 0.65 kW/hr, or less than about 0.6 kW/hr. For example, in certain embodiments the power usage is 0.38 kW/hr. In certain embodiments, the power usage is 0.66 kW/hr. In certain embodiments, the power usage is 0.70 kW/hr.

In certain embodiments, the specific power usage is less than about 5 kWhr/eq mol, less than about 4 kWhr/eq mol, less than about 3 kWhr/eq mol, less than about 2 kWhr/eq mol, less than about 1 kWhr/eq mol, less than about 0.75 kWhr/eq mol, less than about 0.7 kWhr/eq mol, less than about 0.65 kWhr/eq mol, or less than about 0.6 kWhr/eq mol of the cation of the salt of the amino acid. For example, in certain embodiments the specific power usage is 0.084 kWhr/eq mol of the cation of the salt of the amino acid. In certain embodiments, the specific power usage is 0.090 kWhr/eq mol of the cation of the salt of the amino acid. In certain embodiments, the specific power usage is 0.70 kWhr/eq mol of the cation of the salt of the amino acid.

In certain embodiments, the salt of the amino acid constitutes from about 10 wt % to about 20 wt % of the salt stream of the three-compartment electrodialysis bipolar membrane or the two-compartment electrodialysis bipolar membrane and the total power usage required to achieve a target yield of amino acid is less than about 5 kW/hr, less than about 4 kW/hr, or less than about 3 k/Whr.

PMIDA and Glyphosate Production

The amino acid product of the three-compartment BME electrodialysis processes of the present invention can be utilized in processes for preparation of N-(phosphonomethyl)iminodiacetic acid or a salt thereof (i.e., PMIDA). PMIDA can subsequently be converted to N-(phosphonomethyl)glycine or a salt thereof (i.e., glyphosate). FIG. 3 shows an example of such a process wherein "PM" comprises PMIDA and "Gl Cake" comprises glyphosate.

Two-Compartment and Three-Compartment Bipolar Membrane Apparatus Configuration

The present invention is also directed to a process for preparing an amino acid wherein a salt stream comprising a salt of the amino acid is introduced to a two-compartment electrodialysis bipolar membrane cell comprising a salt compartment and a base compartment and the product from the salt compartment of the two-compartment electrodialysis bipolar membrane cell is introduced into the salt compartment of a three-compartment electrodialysis bipolar membrane cell comprising an acid compartment, a salt compartment, and a base compartment. Generally, the three-compartment electrodialysis bipolar membrane cell of this process operates in the manner set forth above with respect to the three-compartment bipolar membrane apparatus. However, use of a two-compartment bipolar membrane cell prior to a three-compartment membrane cell may provide various processing advantages, as detailed below.

The two-compartment electrodialysis bipolar membrane cell generally comprises a bipolar membrane (BPM) and cation exchange membrane (CEM). For example, typically multiple repeating units of BPM-CEM-BPM are placed between two electrodes thereby forming a two-compartment BME cell containing multiple base and salt compartments. In one embodiment, the two-compartment BME cell may comprise one or more repeating units of [BPM-CEM-BPM]$_n$, wherein n can be any whole number from 1 to 200. For example, n can be any whole number from 1 to 100, such as 2, 5, 7, 10, 12, 15, or 20.

Suitable bipolar membrane(s) and cation exchange membrane(s) of the two-compartment electrodialysis bipolar membrane cell may be selected as discussed above with respect to the three-compartment electrodialysis bipolar membrane cell.

Although reference is made herein to the amino acid iminodiacetic acid (IDA) and the amino acid salts disodium iminodiacetic acid (DSIDA) and monosodium iminodiacetic acid (MSIDA), it is understood that the apparatuses and processes described herein are applicable to numerous other amino acids and their salts.

Figure 4:
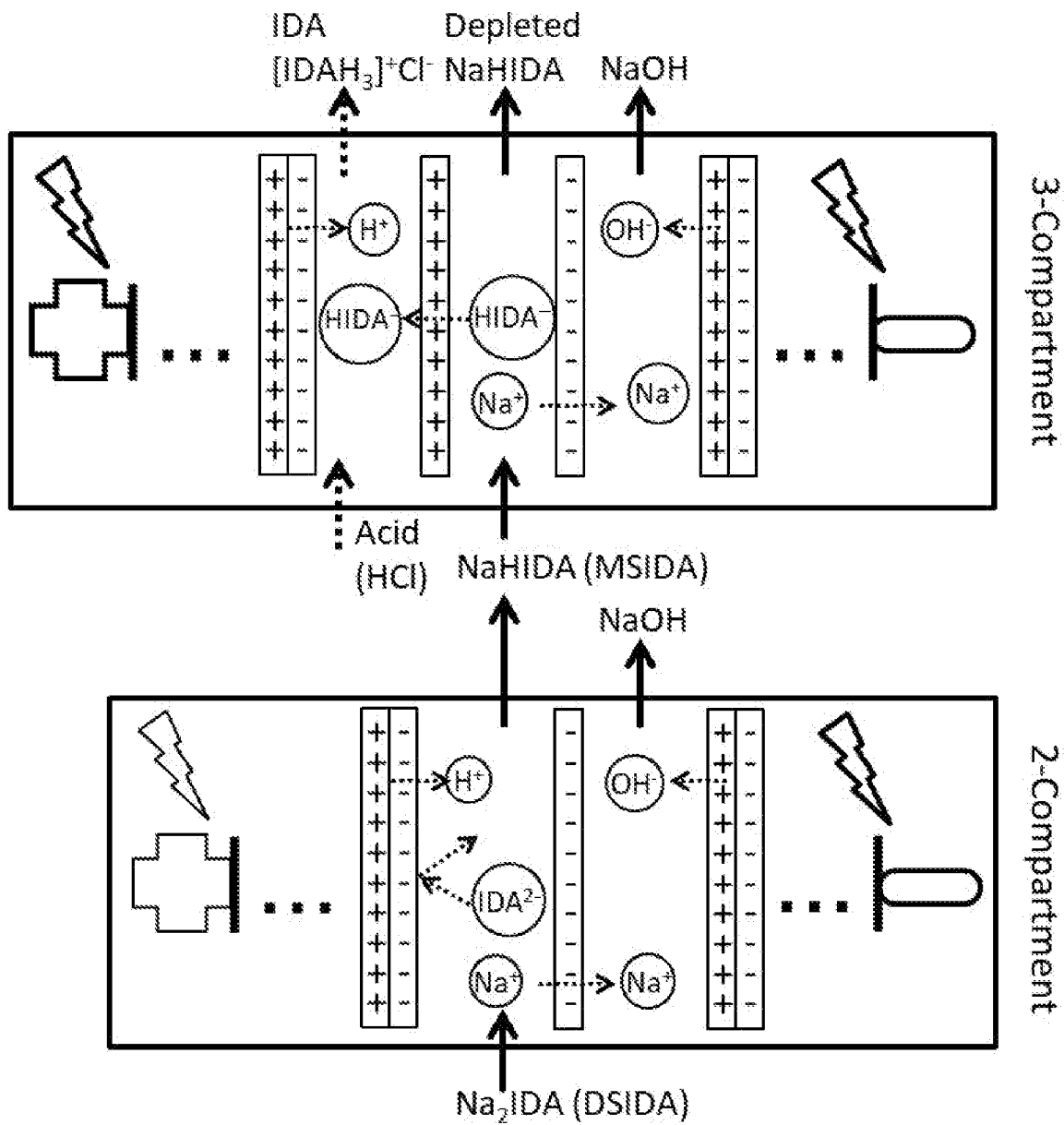
FIG. 4 shows a suitable two-compartment bipolar exchange membrane assembly followed by a three-compartment bipolar exchange membrane assembly.
Figure 5:
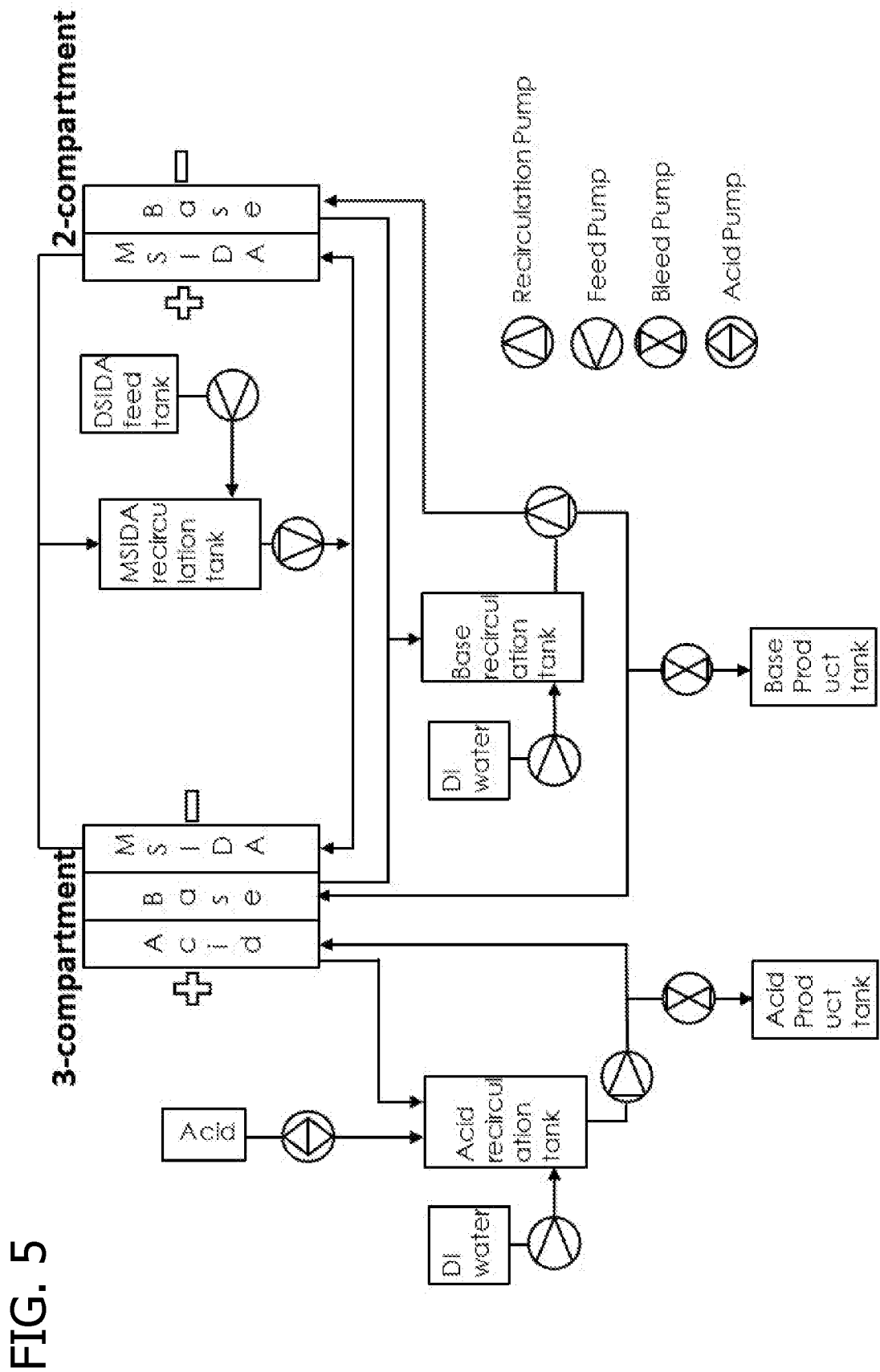
FIG. 5 shows a flow diagram of the combination of a two-compartment bipolar exchange membrane process followed by a three-compartment bipolar exchange membrane process.

In one embodiment, a feed salt stream comprising DSIDA is introduced into the salt compartment of a two-compartment electrodialysis bipolar membrane cell comprising a salt compartment and a base compartment. The resulting product stream of the salt compartment comprises MSIDA, while the resulting product stream of the base compartment comprises NaOH. The NaOH may be recovered for use in other processes (e.g., formation of DSIDA). The MSIDA product from the two-compartment electrodialysis bipolar membrane cell is then introduced into the salt compartment of the three-compartment electrodialysis bipolar membrane cell as the three-compartment electrodialysis bipolar membrane cell "feed salt stream." The process of preparing the amino acid using a three-compartment electrodialysis bipolar membrane cell is then conducted in the manner discussed above with respect to the three-compartment bipolar membrane apparatus. In some embodiments, the MSIDA product of the two-compartment electrodialysis bipolar membrane cell further comprises IDA. This configuration is shown in FIG. 4.

Use of a two-compartment electrodialysis bipolar membrane cell prior to the three-compartment electrodialysis bipolar membrane cell allows for a reduction in power consumption for the three-compartment electrodialysis and lower capital costs (including replacement costs) with respect to the anion exchange membrane.

Further, it has been found that the use of an exogenous acid (e.g., HCl) in the acid compartment of the three-compartment electrodialysis cell as described above may result in the presence of low levels of the exogenous acid anion (e.g., Cl$^-$) in the base compartment product of the three-compartment electrodialysis cell. As greater amounts of exogenous acid are used, the levels of exogenous acid anion contamination of the base compartment product may increase. By first subjecting the salt of the amino acid (e.g., DSIDA) to a two-compartment electrodialysis, a portion of the base product can be produced before the introduction of the exogenous acid and without the exogenous acid anion contamination. In the embodiment shown in FIG. 4, the NaOH produced in the two-compartment electrodialysis cell can be removed from the system as a base compartment product. In some embodiments, up to 50% of the overall base product can be produced in the two-compartment electrodialysis cell, resulting in only 50% of the base product potentially being subject to exogenous acid anion contamination by the three-compartment electrodialysis cell. This provides an added benefit when the bipolar exchange membrane system is used in the context of glyphosate production as shown in FIG. 3. NaOH can be recycled from the bipolar exchange membrane system as a feed stream in the formation of DSIDA. By utilizing a two-compartment electrodialysis cell prior to a three-compartment electrodialysis cell, the portion of the NaOH recovered from the two-compartment electrodialysis cell does not need to be further processed before being recycled to the process for forming DSIDA.

Further, the use of a two-compartment electrodialysis bipolar membrane cell prior to the three-compartment electrodialysis bipolar membrane cell allows for narrower pH variations within the anion exchange membrane component of the three-compartment electrodialysis bipolar membrane cell. For example, without the use of two-compartment electrodialysis the pH of the salt compartment of the three-compartment bipolar membrane cell in some embodiments is at least about 8, at least about 9, at least about 9.5, at least about 10, at least about 10.5, at least about 11, at least about 11.5, or at least about 12. However, initially subjecting the salt of the amino acid to two-compartment electrodialysis can result in a pH of about 6 in the salt compartment of the three-compartment electrodialysis bipolar membrane cell. For example, a pH of at least about 6, at least about 7, or from about 6 to about 8, or from about 7 to about 8. This reduction in pH of the salt compartment allows for more flexibility in the type of membrane used and overall membrane longevity.

EXAMPLES

Example 1

An experiment was performed to evaluate the production of iminodiacetic acid (IDA) from a feed stream comprising disodium iminodiacetic acid (DSIDA) utilizing a three-compartment bipolar membrane electrodialysis process.

The experiment utilized a feed stream comprising 10 wt % DSIDA wherein the membrane was a Neosepta anionic exchange membrane (AEM) commercially available from Astom (Tokyo, Japan). The bipolar membrane cell consisted of 7 repeating membranes units of [BPM-AEM-CEM]. The pH of the acid compartment was maintained at a value of about 1 by the addition of exogenous HCl. The electrodialysis process was run for a period of 110 minutes.

A calculation of the $Na^+$ cations transferred was performed based on a comparison of the molar amount of $Na^+$ cations present in the feed stream to the molar amount of $Na^+$ cations present in the base compartment. For example, (moles of $Na^+$ recovered in the base compartment)/(moles of $Na^+$ in DSIDA feed)×100.

The percentage of $Na^+$ cations removed from the feed was calculated by comparing the molar amount of $Na^+$ cations present in the feed stream to the molar amount of $Na^+$ cations present in the stream exiting the salt compartment. For example, [(moles of $Na^+$ in DSIDA feed)−(moles of $Na^+$ recovered in exit stream of the salt compartment)]/(moles of $Na^+$ in DSIDA feed)×100.

The NaOH yield was calculated based on a comparison of the molar amount of $Na^+$ cations present in the feed stream to the moles of NaOH recovered in the base compartment. For example, (moles NaOH recovered from base compartment)/(moles $Na^+$ in DSIDA feed)×100.

Likewise, the percentage of IDA anions transferred was calculated based on a comparison of the molar amount of iminodiacetic acid$^{-2}$ anions present in the feed stream to the molar amount of iminodiacetic acid$^{-2}$ anions present in the acid compartment. For example, (moles of iminodiacetic acid$^{-2}$ recovered in the acid compartment)/(moles of iminodiacetic acid$^{-2}$ in DSIDA feed)×100.

The amount of IDA removed from the feed stream was determined by comparing the molar amount of iminodiacetic acid$^{-2}$ anions present in the feed stream to the molar amount of iminodiacetic acid$^{-2}$ anions present in the stream exiting the salt compartment. For example, [(moles of iminodiacetic acid$^2$ in DSIDA feed)−(moles of iminodiacetic acid$^{-2}$ recovered in exit stream of the salt compartment)]/(moles of iminodiacetic acid$^{-2}$ in DSIDA feed)×100.

An IDA yield was also calculated based on a comparison of the molar amount of iminodiacetic acid$^{-2}$ anions present in the feed stream to the moles of iminodiacetic acid recovered in the acid compartment. For example, (moles iminodiacetic acid recovered from acid compartment)/(moles iminodiacetic acid$^{-2}$ in DSIDA feed)×100.

The process conditions and results are outlined below in Table 1.

TABLE 1

| | |
|---|---|
| Initial DSIDA wt % in Salt Chamber | 10 wt % |
| Anion Exchange Membrane | Neosepta |
| Power Usage (kW-hr) | 0.38 |
| Specific Power Usage (kW-hr/eq mol $Na^+$) | 0.084 |
| Current Efficiency based on $Na^+$ Transport | 90% |
| NaOH yield | 100.8% |
| IDA yield | 99.4% |

Figure 6:
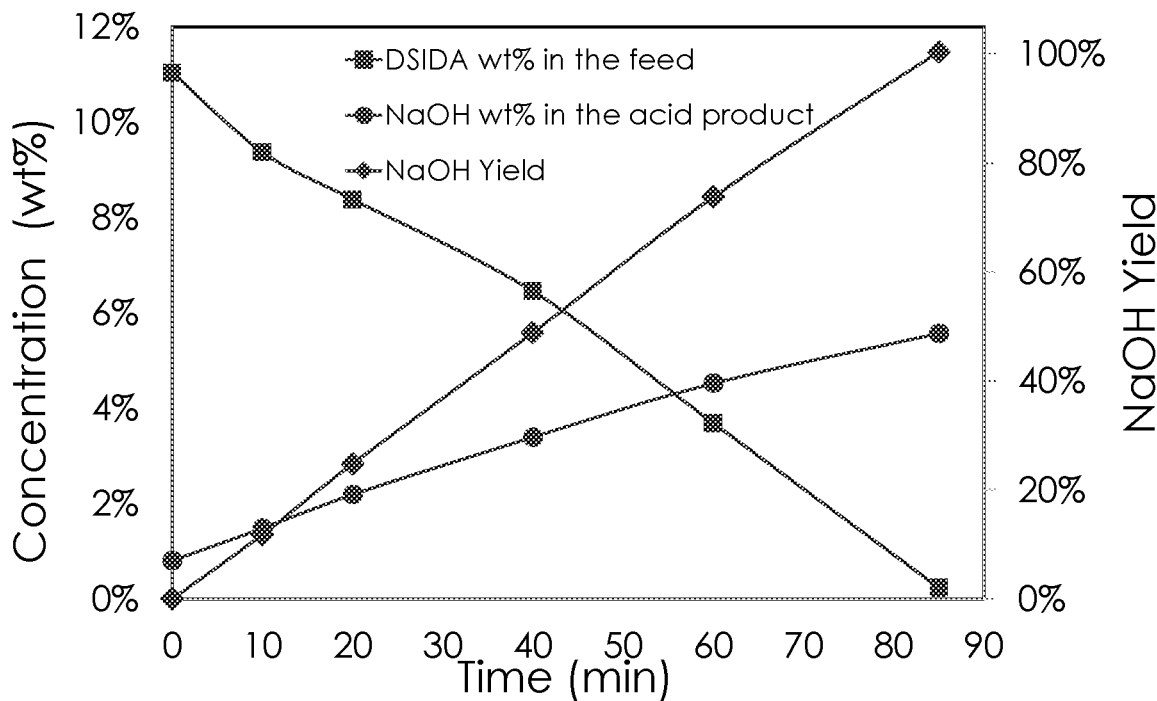
FIG. 6 shows the concentration of DSIDA, concentration of NaOH, and NaOH yield of Example 1.

FIG. 6 illustrates the change in concentration in the feed (i.e., salt) and base compartments. The concentration of DSIDA on a weight basis in the salt compartment steadily decreases over time, to a value of about 0 wt % at the conclusion of the experiment. This indicates that the iminodiacetic acid$^{-2}$ anions from the DSIDA feed stream have been transported though the membrane wall of the salt compartment and towards the anode, while cations from the DSIDA feed stream (e.g., $Na^+$) have been transported through the membrane wall of the salt compartment toward the cathode. The increased concentration of NaOH in the base compartment over time is a further indication that the cations from the DSIDA feed stream (e.g., $Na^+$) have been transported through the membrane wall of the salt compartment into the base compartment. In the base compartment, the cations from the DSIDA feed stream ($Na^+$) combine with the $OH^-$ present from the water splitting operation of the bipolar membrane to form NaOH. The NaOH yield is calculated as described above. As expected, a decrease in DSIDA concentration in the salt compartment coupled with an increase of base present in the base compartment results in an increasing amount of NaOH yield over time. As the concentration of DSIDA in the salt compartment approaches zero the NaOH yield approaches a constant value, indicating the maximum achievable yield of the tested system has been achieved.

Figure 7:
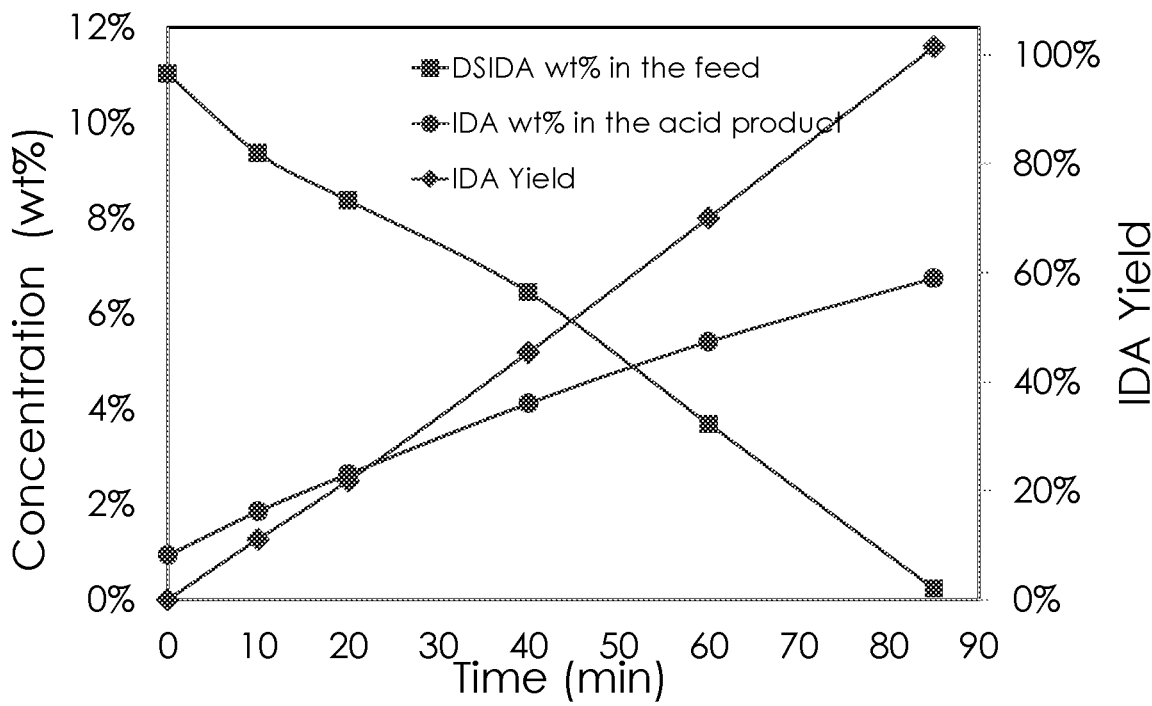
FIG. 7 shows the concentration of DSIDA, concentration of IDA, and IDA yield of Example 1.

FIG. 7 plots the change in concentration of the salt compartment and acid compartment of the 10 wt % DSIDA feed. The change in DSIDA concentration is discussed above. The concentration of IDA in the acid compartment increases over time. This increased concentration indicates that the anions from the DSIDA feed stream (e.g., iminodiacetic acid$^{-2}$) have been transported though the membrane wall of the salt compartment and towards the acid compartment. In the acid compartment, the anions from the DSIDA feed stream combine with the $H^+$ present from the water splitting operation of the bipolar membrane to form IDA as shown in FIG. 1b. As expected, a decrease in DSIDA concentration in the salt compartment coupled with an increase of IDA in the acid compartment results in an increasing amount of IDA yield over time.

Figure 8:
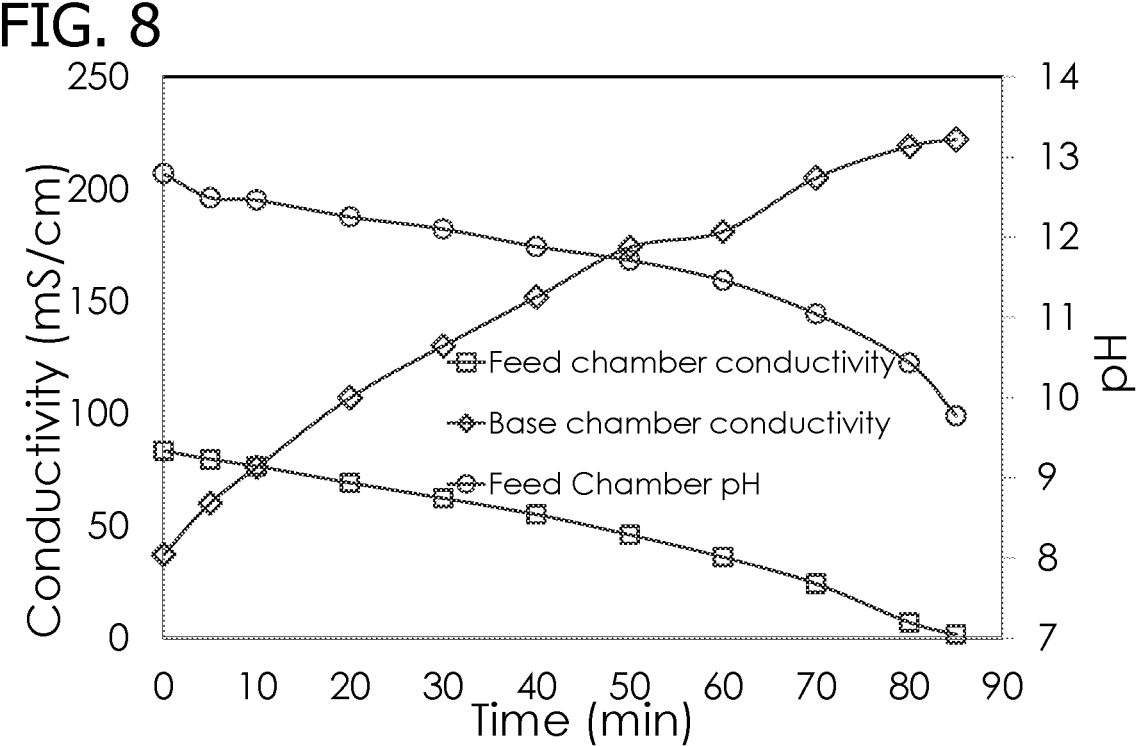
FIG. 8 shows the conductivity of the content of the feed (salt) compartment and base compartment and the feed (salt) compartment pH of Example 1.

FIG. 8 is a graphical representation of the change in conductivity of the contents of the feed (salt) and base compartments, as well as the change in salt compartment pH over time. The feed (salt) compartment content conductivity trends towards 0 mS/cm over the course of the experiment. This indicates that the anions from the DSIDA feed stream (e.g., iminodiacetic acid$^{-2}$) have been transported though the membrane wall of the salt compartment and towards the anode, while cations from the DSIDA feed stream (e.g., Na$^+$) have been transported through the membrane wall of the salt compartment toward the cathode. As the respective anions and cations are removed from the salt compartment, the remaining solution within the salt compartments comprises only the feed components other than DSIDA (generally water). As the main component in the feed stream is water, a near zero conductivity is observed. This phenomenon also explains the why pH within the feed (salt) compartment trends towards a value of 7 over the course of the experiment. Conversely, the conductivity of the content of the base compartment increases over time as cations from the DSIDA feed stream (e.g., Na$^+$) are transported through the membrane wall of the salt compartment and into the base compartment. At the same time, the cations from the DSIDA feed stream combine with the OH$^-$ present from the water splitting operation of the bipolar membrane to form NaOH. The composition of the base compartment evolves from a solution comprised mainly of water to a solution containing increasing amounts of NaOH.

Figure 9:
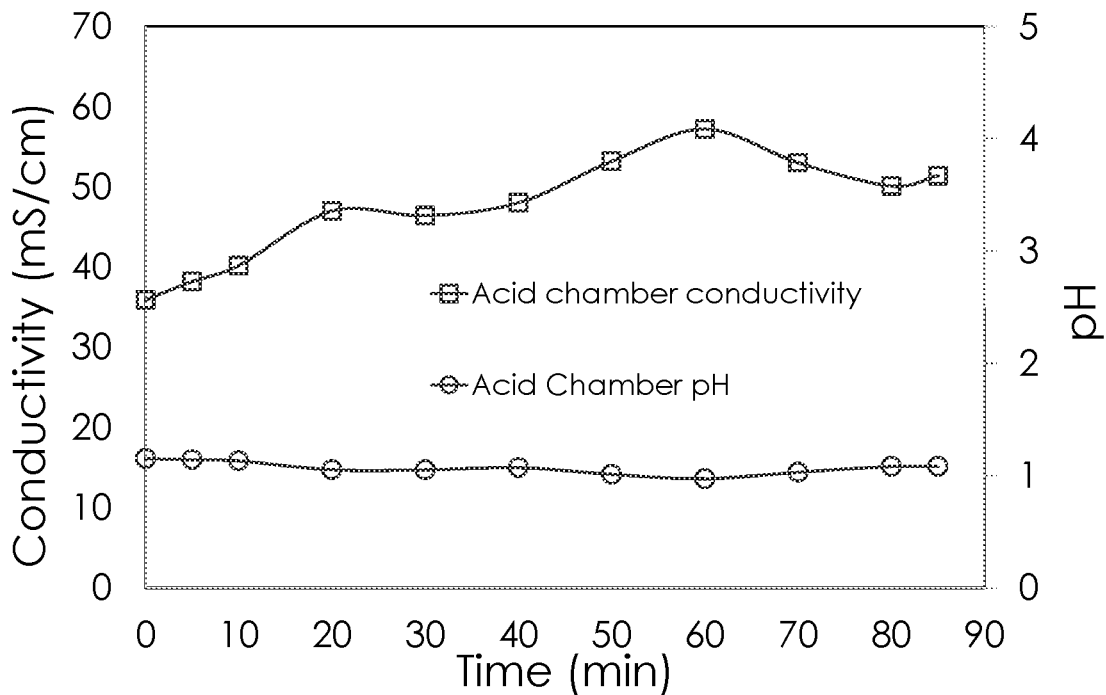
FIG. 9 shows the conductivity and pH of the contents of the acid compartment of Example 1.

FIG. 9 shows a graphical representation of the change in conductivity and pH of the contents of the acid compartment over the course of the experiment. As described above, the iminodiacetic acid$^{-2}$ anions from the DSIDA feed stream are transported though the membrane wall of the salt compartment towards the acid compartment and the anions from the DSIDA feed stream combine with the H$^+$ present from the water splitting operation of the bipolar membrane to form IDA. The acid compartment was charged with a solution of strong acid (i.e., an aqueous electrolyte comprising an acid), resulting in the relatively low starting pH. As noted above, the pH was maintained at a pH of about 1 by introduction of additional strong acid to the acid compartment. As the anions from the DSIDA feed stream are transported into the acid compartment and form IDA, a higher concentration of IDA within the acid compartment is observed. This results in a moderate increase in the observed conductivity of the acid chamber contents.

Figure 10:
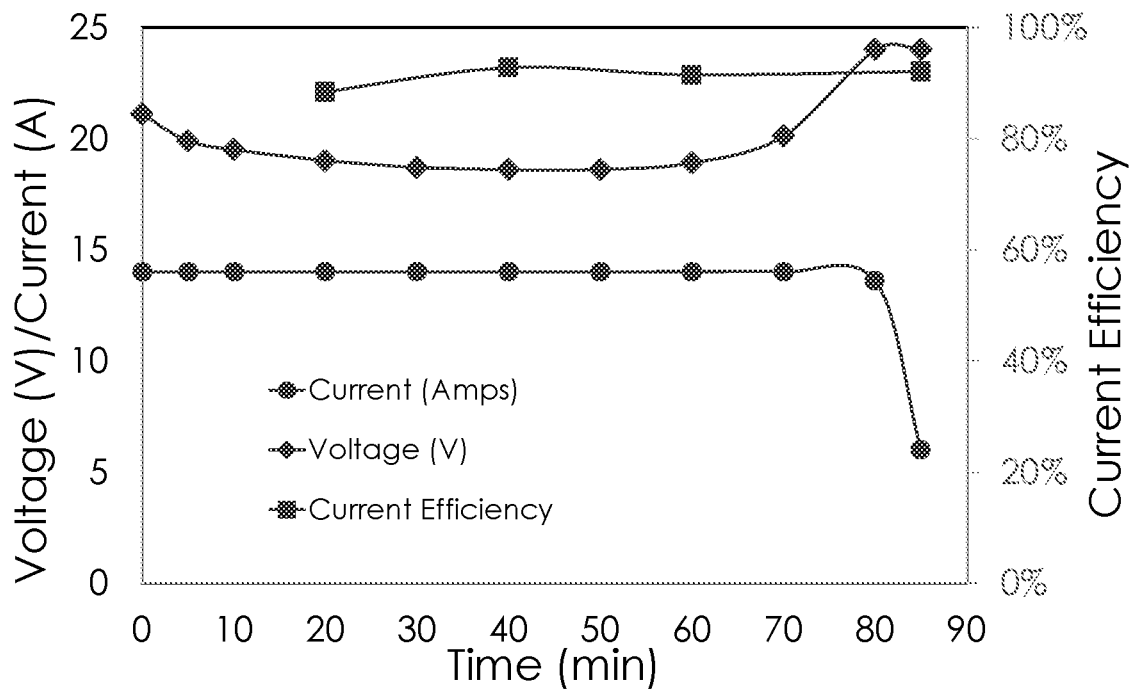
FIG. 10 shows the evolution of current, voltage, and current efficiency of Example 1.

FIG. 10 shows the evolution of current, voltage, and current efficiency during the course of the experiment.

Example 2

A further experiment similar to Example 1 was performed utilizing a 20 wt % DSIDA feed solution. The anion exchange membrane used was a Neosepta anionic exchange membrane commercially available from Astom (Tokyo, Japan). The acid compartment was maintained at a pH of about 0.7 and a temperature of about 35° C.

The process conditions and results are outlined below in Table 2.

TABLE 2

| | |
|---|---|
| Initial DSIDA wt % in Salt Chamber | 20 wt % |
| Anion Exchange Membrane | Neosepta |
| Power Usage (kW-hr) | 0.66 |
| Specific Power Usage (kWhr/eq mol Na$^+$) | 0.090 |
| Current Efficiency based on Na$^+$ Transport | 89% |

TABLE 2-continued

| | |
|---|---|
| NaOH yield | 94.2% |
| IDA yield | 96.5% |

Figure 11:
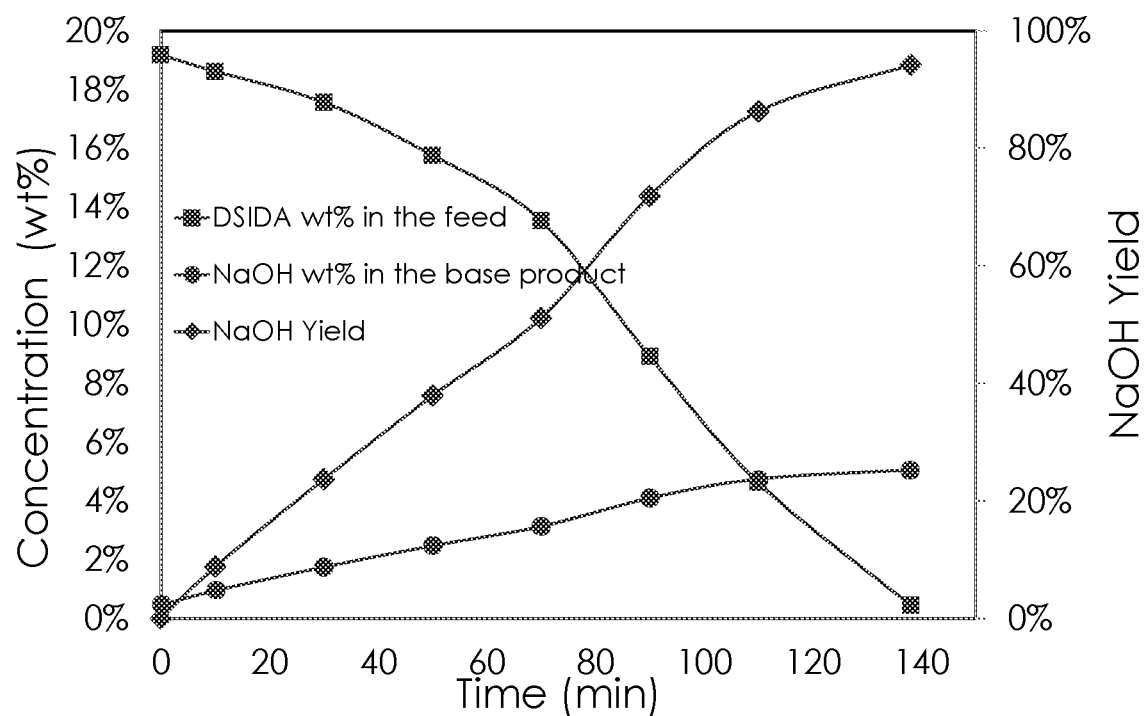
FIG. 11 shows the concentration of DSIDA, concentration of NaOH, and NaOH yield of Example 2

FIG. 11 illustrates the changes in concentration of the feed (i.e. salt) and base compartments, as discussed above with respect to Example 2.

Figure 12:
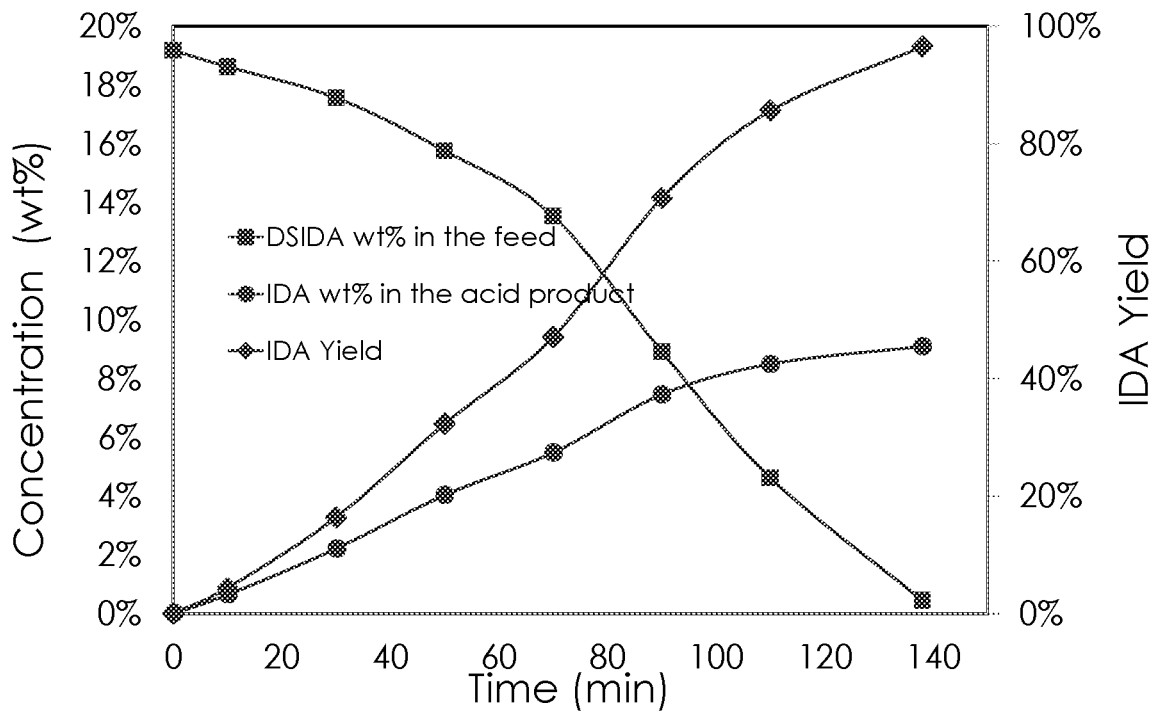
FIG. 12 shows the concentration of DSIDA, concentration of IDA, and IDA yield of Example 2.

FIG. 12 illustrates the changes in concentration of the DSIDA in the feed (salt) compartment and IDA in the acid compartment. FIG. 12 also shows the IDA yield as a function of time.

Figure 13:
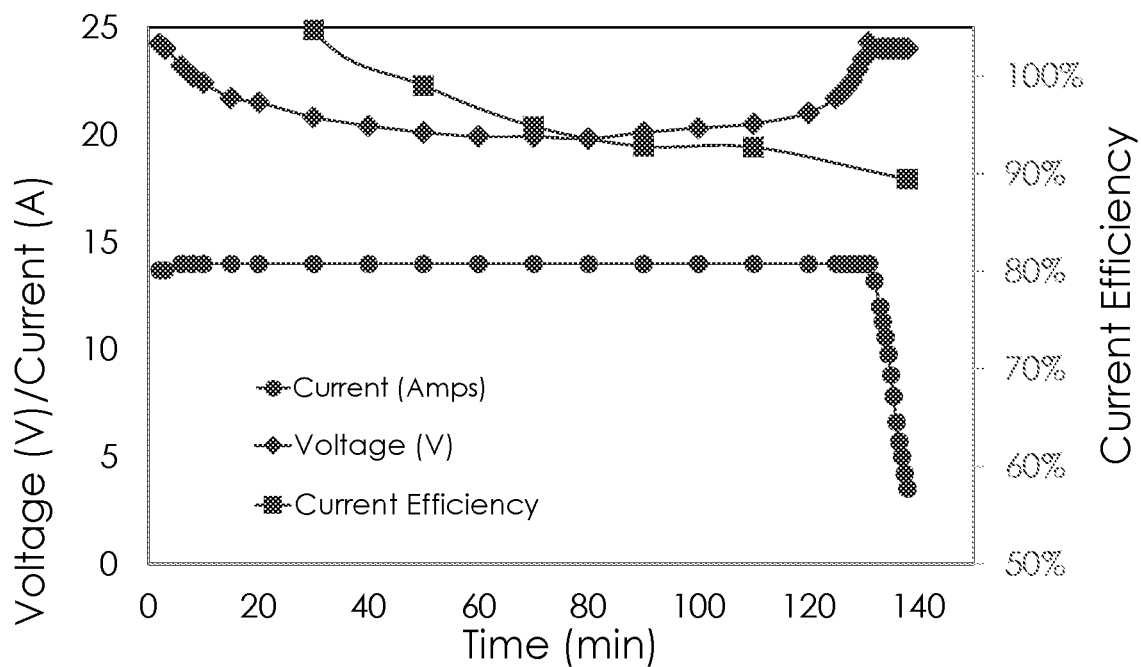
FIG. 13 shows the current efficiency as well as the current and voltage applied across the membrane stack of Example 2.

FIG. 13 illustrates the evolution of current, voltage, and current efficiency as a function of time.

Example 3

A further experiment similar to Example 2 was performed utilizing a 20 wt % DSIDA feed solution and a NEOSEPTA anion exchange membrane (commercially available from Astom Corp.).

The process conditions and results are outlined below in Table 3.

TABLE 3

| | |
|---|---|
| Initial DSIDA wt % in Salt Chamber | 20 wt % |
| Anion Exchange Membrane | Neosepta |
| Power Usage (kW-hr) | 0.70 |
| Specific Power Usage (kWhr/eq mol Na$^+$) | 0.094 |
| Current Efficiency based on Na$^+$ Transport | 89% |
| NaOH yield | 98.2% |
| IDA yield | 97.4% |

Figure 14:
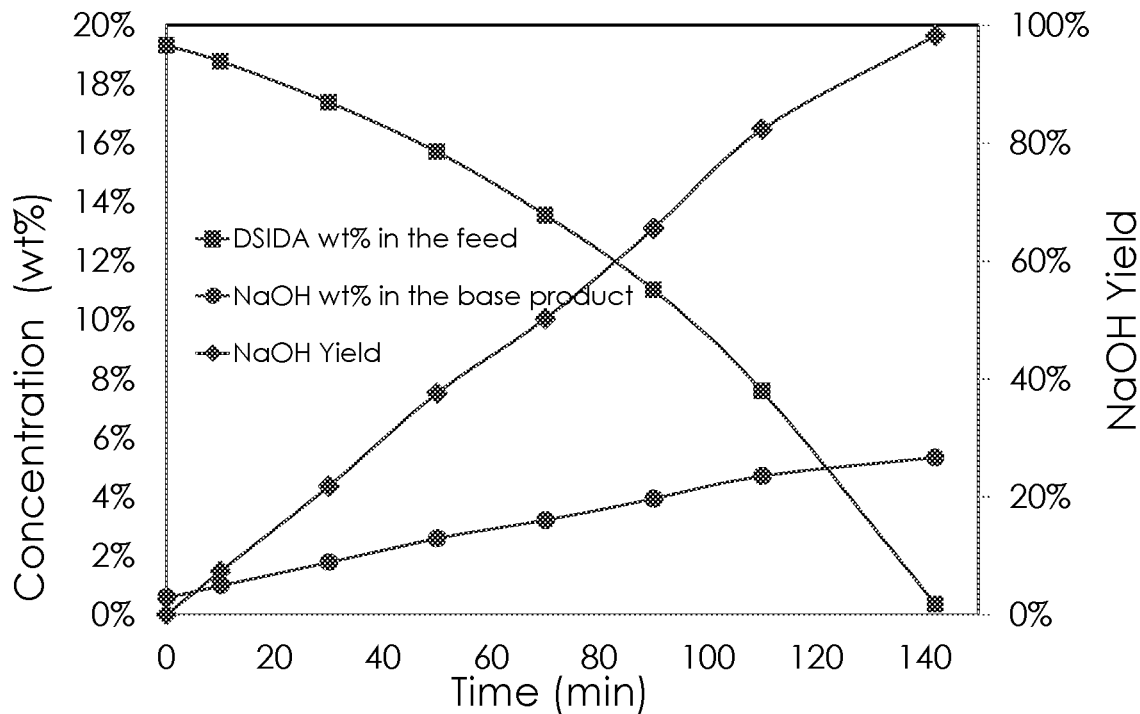
FIG. 14 shows the concentration of DSIDA, concentration of NaOH, and NaOH yield of Example 3.

FIG. 14 illustrates the changes in concentration of the feed (i.e. salt) and base compartments. FIG. 14 also reports the NaOH yield as a function of time.

Figure 15:
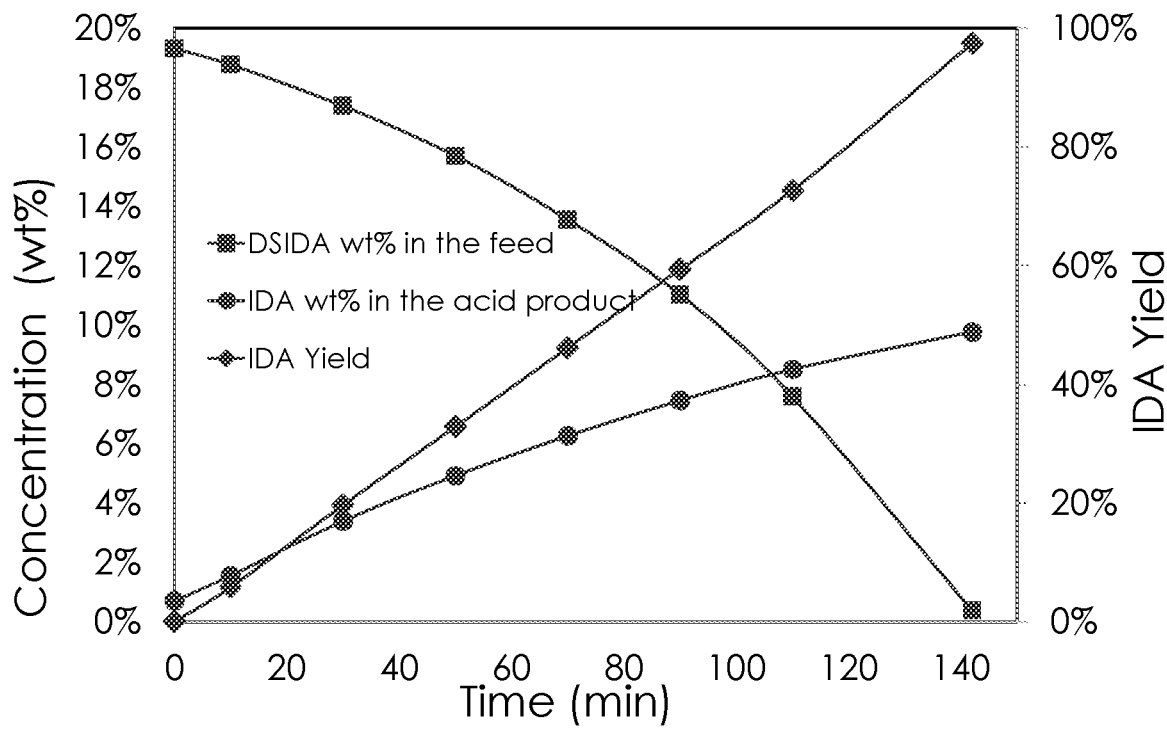
FIG. 15 shows the concentration of DSIDA, concentration of IDA, and IDA yield of Example 3.

FIG. 15 illustrates the changes in concentration of the feed (i.e. salt) and acid compartments as well as the IDA yield.

Figure 16:
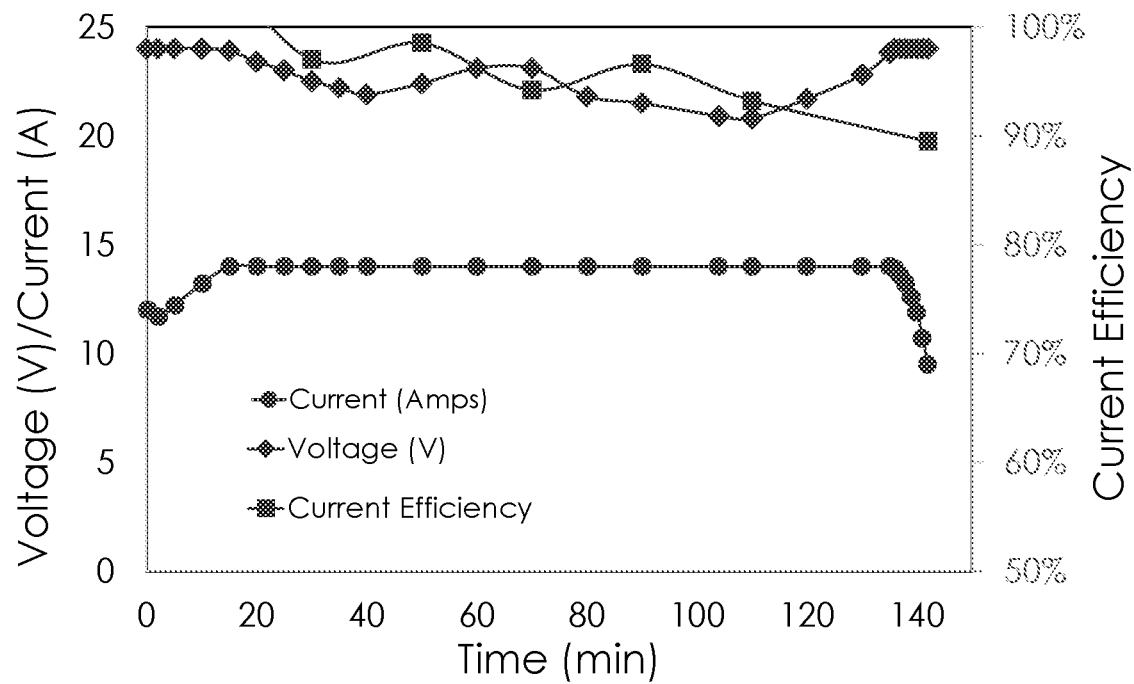
FIG. 16 shows the current efficiency as well as the current and voltage applied across the membrane stack of Example 3.

FIG. 16 illustrates the evolution of current, voltage, and current efficiency of Example 3.

Table 4 below illustrates the comparative power usage, specific power usage, current efficiency, and NaOH and IDA yield for each of Examples 1-3.

TABLE 4

| | Example 1 | Example 2 | Example 3 |
|---|---|---|---|
| Initial DSIDA wt % in Salt Chamber | 10 wt % | 20 wt % | 20 wt % |
| Anion Membrane Type | Neosepta | Neosepta | Neosepta |
| Power Usage (kW-hr) | 0.38 | 0.66 | 0.70 |
| Specific Power Usage (kW-hr/eq mol Na$^+$) | 0.084 | 0.090 | 0.094 |
| Current Efficiency based on Na$^+$ Transport | 90% | 89% | 89% |
| NaOH yield | 100.8% | 94.2% | 98.2% |
| IDA yield | 99.4% | 96.5% | 97.4% |

Example 4: Continuous Feed Experiment

Figure 17:
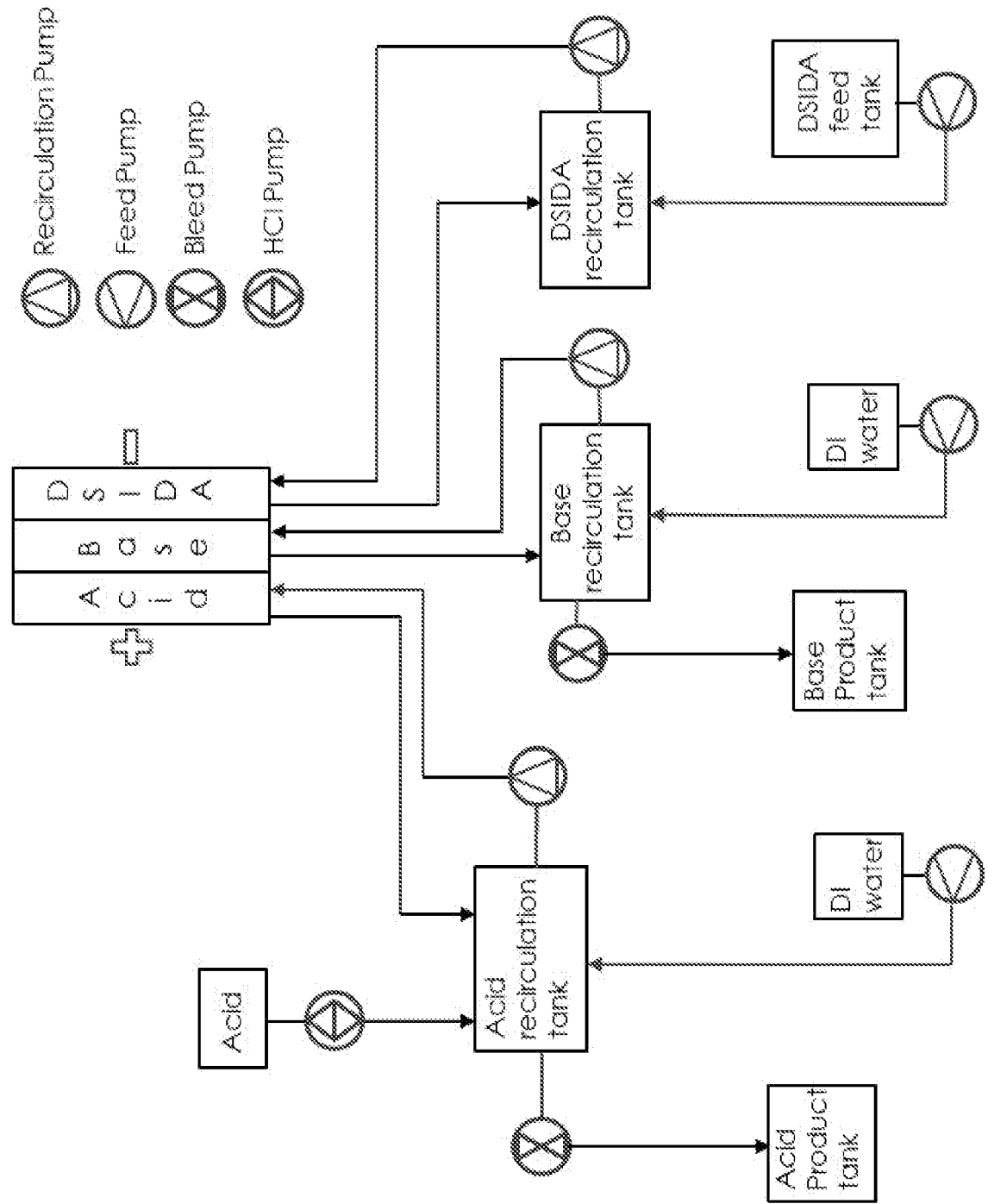
FIG. 17 shows a flow diagram of a three-compartment bipolar membrane electrodialysis cell, including recirculation of product streams and introduction of the feed stream(s) through the recirculation tank(s).

A continuous feed experiment was performed where DSIDA was continuously fed into the salt (feed) compartment. FIG. 17 shows a flow diagram of the continuous feed process. The product stream of each compartment is sent through a recirculation tank wherein some of the product stream is optionally recirculated to the respective compartments and/or recovered in a subsequent product tank. Exogenous acid is added to the acid compartment recirculation tank and introduced to the acid compartment by means of the acid compartment recirculation pump. DSIDA feed and deionized water are added in a similar manner to the respective recirculation tanks.

The pH of the acid compartment was maintained at approximately 0.7 and the temperature was maintained at approximately 37° C. A feed stream having 28 wt % DSIDA was fed into the salt (feed) compartment via the DSIDA recirculation tank at a rate of 15 g/min. The base compartment feed/bleed rate was maintained at approximately 20 g/l in order to ensure a NaOH concentration in the base product stream of approximately 8.5 wt %. The feed/bleed rate for the acid compartment was maintained at approximately 18 g/l in order to ensure an IDA product concentration of approximately 14 wt % in the acid product stream. At the conclusion of each run (approximately every 5-6 hours), all solutions in each chamber were drained and collected. Following the removal of the contents of each chamber, deionized water was introduced into each compartment. Before beginning the next run, the solutions from the previous run were reintroduced into their respective compartments. This procedure was repeated for a total experiment duration of approximately 34 hours.

Figure 18:
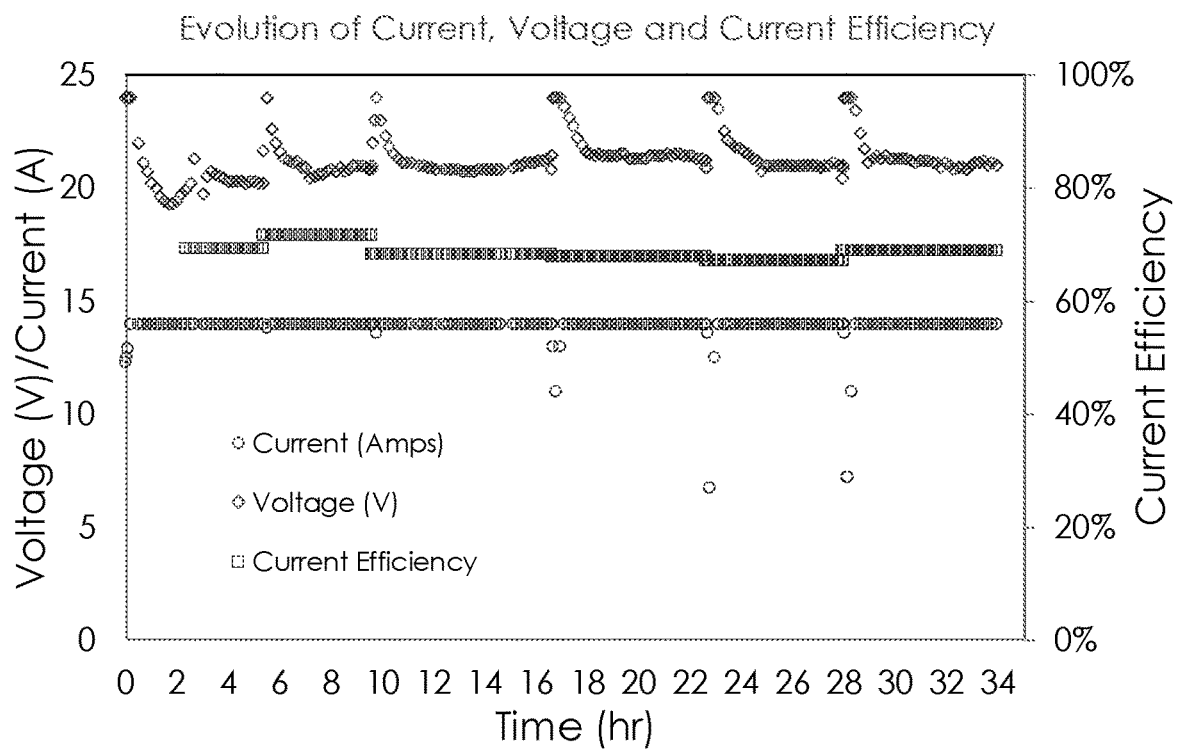
FIG. 18 shows the current, voltage, and current efficiency of Example 4.
Figure 19:
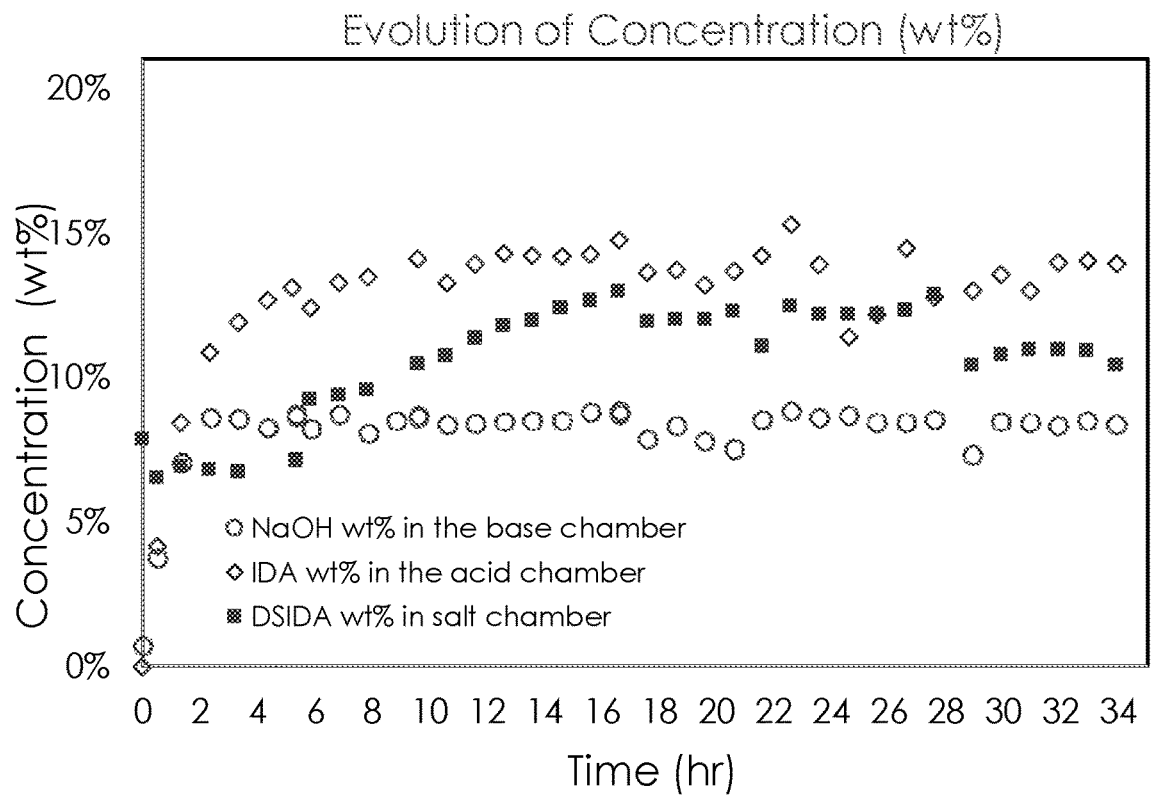
FIG. 19 shows the concentration of NaOH, concentration of IDA, and concentration of DSIDA of Example 4.

FIG. 18 shows the evolution of current, voltage, and current efficiency throughout the process. The concentrations of NaOH in the base compartment, IDA in the acid compartment, and DSIDA in the salt (feed) compartment during the experiment are reported in FIG. 19.

Example 5: Two-Compartment Bipolar Membrane Electrodialysis

An experiment was performed to evaluate the effect of a two-compartment bipolar membrane electrodialysis (BME) process on the amino acid salt disodium iminodiacetic acid (DSIDA).

A laboratory BME membrane system was prepared comprising a membrane stack of 7 membrane cells and two nickel electrodes. The membrane cells contained two compartments, a base and a salt compartment. The cells were comprised of a bipolar membrane (BPM) and a cation exchange membrane (CEM) in the configuration BPM-CEM-BPM.

An aqueous solution comprising DSIDA (approximately 20 wt %) was charged into the salt compartment and diluted NaOH (0.1 M) was charged into the base compartment. The pH and conductivity of the salt compartment was monitored until the pH dropped to between about 7 and about 7.5 and the conductivity dropped to between about 40 and about 45 mS/cm. At this point, approximately 80% of the volume of the salt compartment was removed and labeled as a "MSIDA" (monosodium iminodiacetic acid) product. A 20% solution of DSIDA was then charged to the salt compartment. Once the base compartment reached a conductivity of between about 300 and about 320 mS/cm, indicating the target NaOH concentration, about 80% of the volume of the base compartment was removed and labeled as the "base product." Deionized water in a volume equal to the amount of base product removed was reintroduced into the base compartment. This process was repeated over the course of approximately 25 hours.

Figure 20:
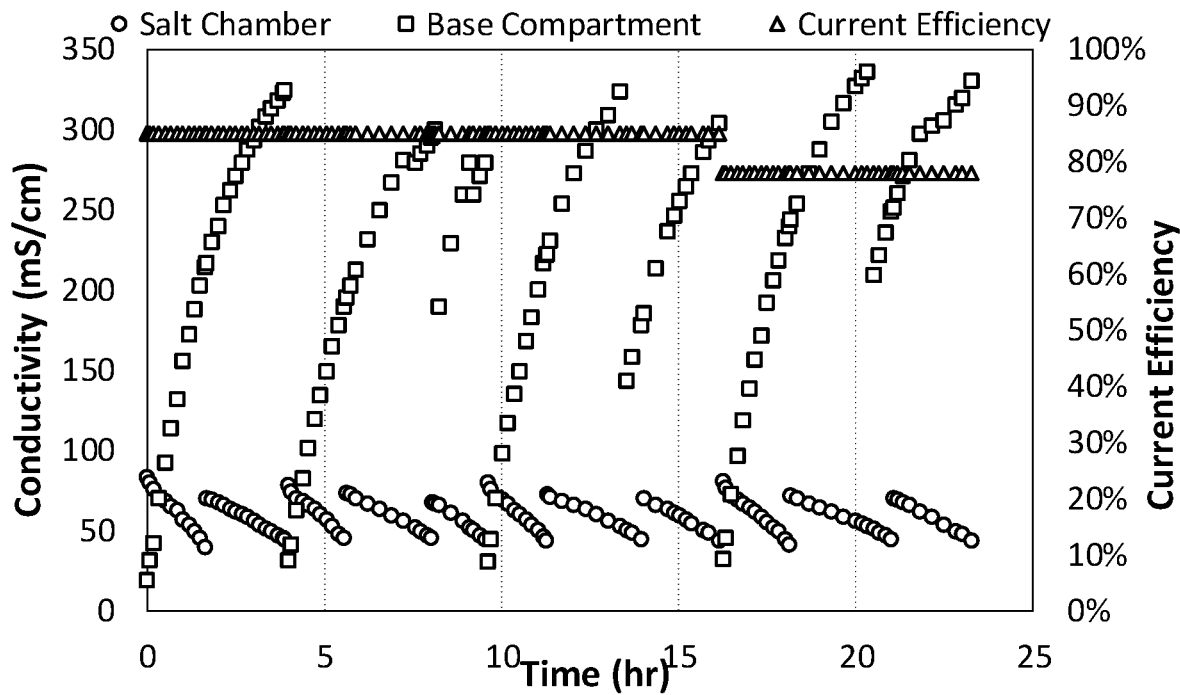
FIG. 20 shows the conductivity and current efficiency of the base and salt compartment of the two-compartment bipolar exchange membrane process of Example 5.

FIG. 20 shows the evolution of the conductivity and current efficiency of the base and salt compartments of the two-compartment BME configuration.

The initial salt compartment conductivity when charged with DSIDA was approximately 80 mS/cm. The conductivity began to decline as the DSIDA was converted to MSIDA. At a conductivity of approximately 45 mS/cm the majority of DSIDA had been converted to MSIDA and the "MSIDA product" was removed. Similarly, the conductivity of the base compartment shown in FIG. 20 indicates the points at which base product was removed and deionized water was added. For example, the first base product was removed at approximately 4.5 hours when the conductivity reached about 325 mS/cm.

Figure 21:
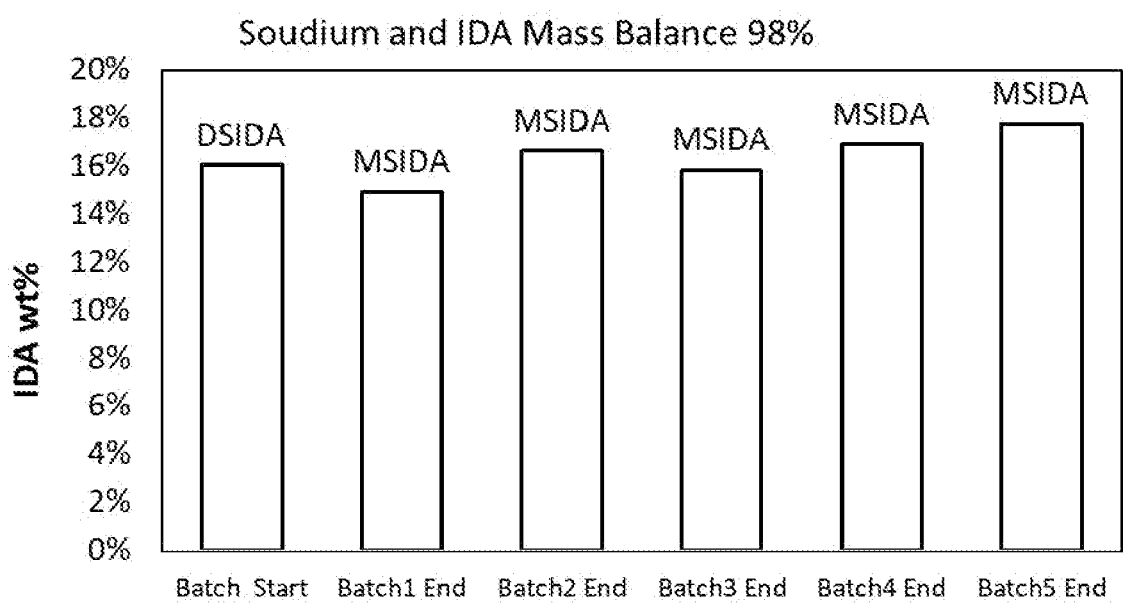
FIG. 21 shows the mass balance and yield of sodium and IDA for the two-compartment bipolar exchange membrane process of Example 5.

FIG. 21 details the initial DSIDA content and the MSIDA concentrations at the end of each batch run. The NaOH product removed from the base compartment varied from about 8.5 wt % to about 10.5 wt %. Overall, an approximately 98% mass balance of sodium and iminodiacetic acid (IDA) was achieved during the two-compartment electrodialysis process.

Figure 22:
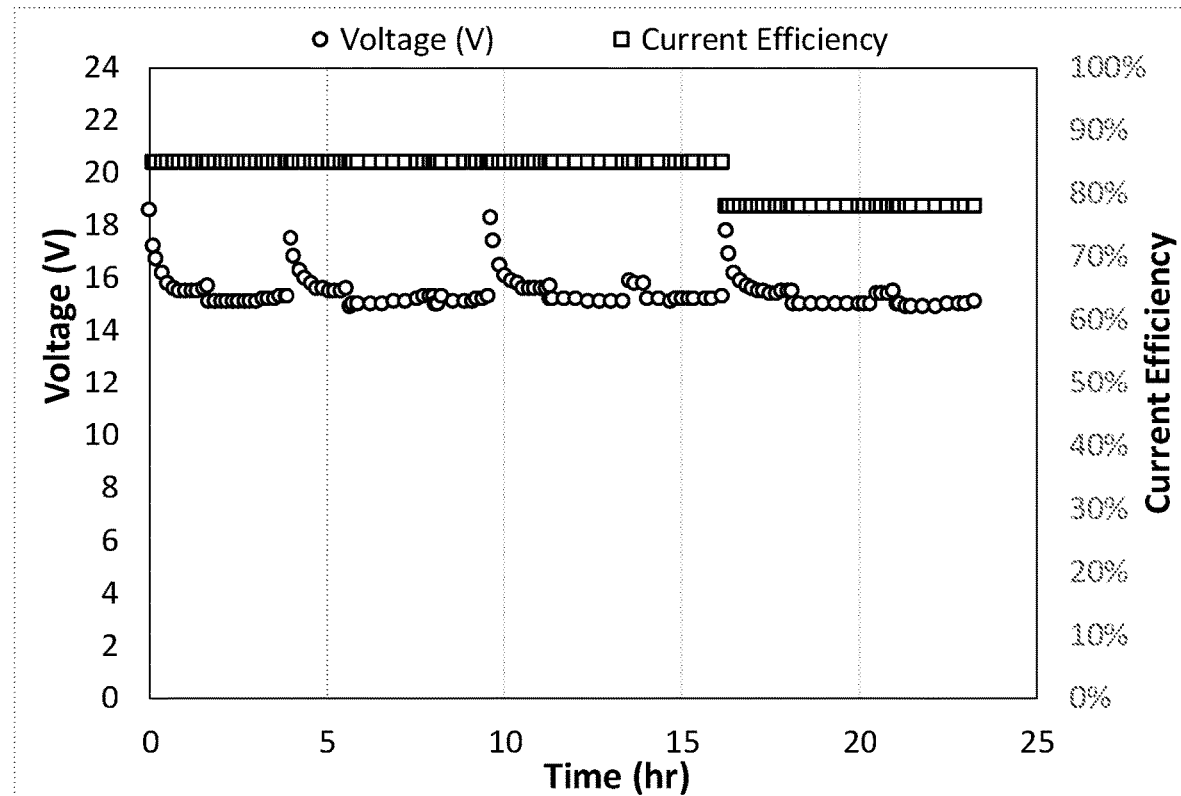
FIG. 22 shows the voltage and current efficiency of the two-compartment bipolar exchange membrane process of Example 5.

The current efficiency achieved by this process was between about 80 and 85%. FIG. 22 illustrates the current efficiency of the process as compared to the voltage. During the entire process, the current was maintained at 14A.

Example 6: Three-Compartment Electrodialysis Using MSIDA from Example 5

The MSIDA product of Example 5 was used as the feed solution for the salt compartment of a three-compartment electrodialysis system comprising a membrane stack having 7 cells and two nickel electrodes. Each membrane cell of the three-compartment electrodialysis system consisted of a base, acid, and salt compartment. The three-compartment membrane cell was substantially the same as described in Example 1.

MSIDA produced in Example 5 (approximately 17 wt % IDA) was continuously introduced into the salt compartment to maintain sufficient IDA strength in the salt loop. There was no continuous feed for the acid or base compartments. The base compartment was charged with 0.1 M NaOH. The acid compartment was charged with 1-2% IDA and was controlled at a pH of 0.8 using 8 M HCl. As the base and acid compartments reached the target concentration, the experiment was stopped and the base and acid products were collected.

Figure 23:
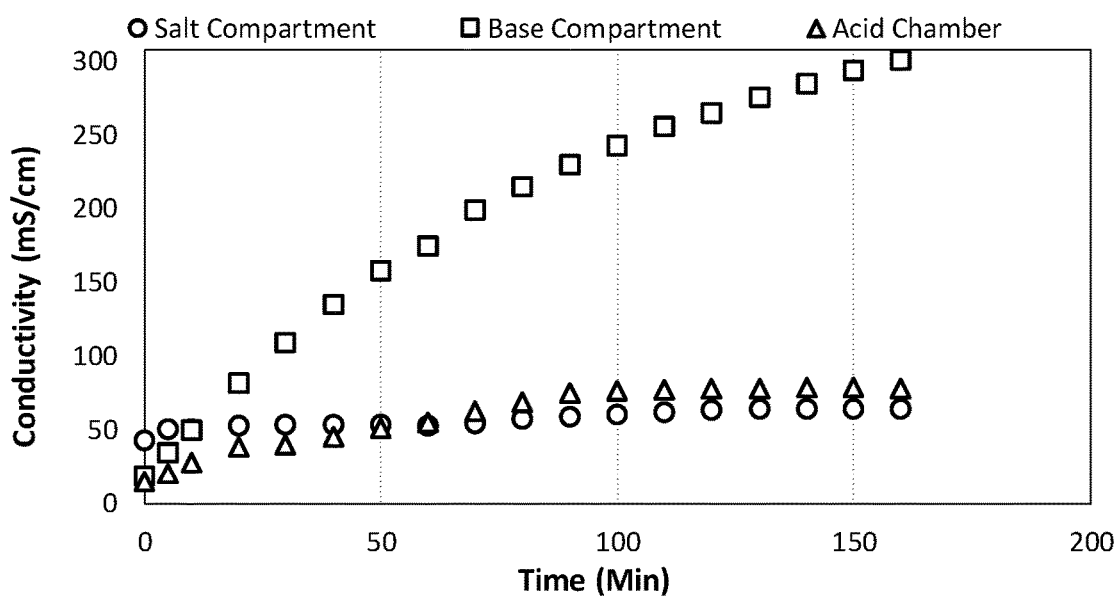
FIG. 23 shows the conductivity of the acid, base, and salt compartment of the three-compartment bipolar exchange membrane process of Example 6.
Figure 24:
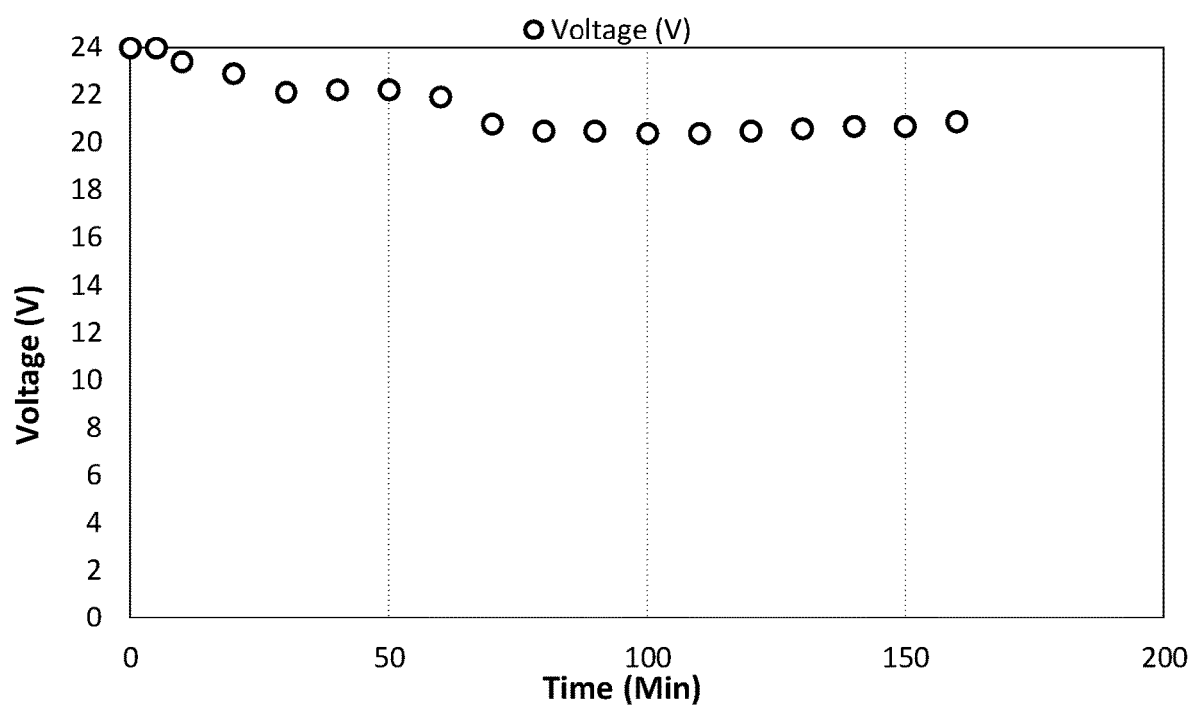
FIG. 24 shows the voltage of the three-compartment bipolar exchange membrane process of Example 6.

FIG. 23 reports the change in conductivity of the acid, base, and salt compartments in the three-compartment BME process. FIG. 24 reports the change in voltage of the three-compartment BME process. During the entire process, the current was maintained at 14A.

At the conclusion of the experiment, the concentration of NaOH in the product from the base compartment was 8.9 wt % and the concentration of the IDA in the product from the acid compartment was 14.3 wt %. Overall, the current efficiency of this experiment was 87%.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and the associated drawings shall be interpreted as illustrative and not in a limiting sense.

What is claimed is:

1. A process for preparing an amino acid, the process comprising:
   introducing an aqueous electrolyte comprising a first acid into an acid compartment of a three-compartment electrodialysis bipolar membrane cell comprising an acid compartment, a salt compartment, and a base compartment;
   introducing a feed salt stream comprising a salt of the amino acid into the salt compartment of the three-compartment bipolar membrane cell, wherein the salt of the amino acid is formed by reacting an amino acid with a base; and
   introducing an aqueous stream into the base compartment of the three-compartment bipolar membrane cell;
   wherein the first acid and the amino acid are different, and the amino acid has a pKa greater than 2.0 and the first acid introduced into the acid compartment of the three-compartment bipolar membrane cell has a pKa less than the pKa of the amino acid, and wherein:
   the three-compartment bipolar membrane cell further comprises a cathode and an anode, the process further comprising applying an electric potential between the cathode and the anode.

2. The process as set forth in claim 1, wherein the amino acid has a pKa greater than 2.5 and the first acid introduced into the acid compartment of the three-compartment bipolar membrane cell has a pKa less than the pKa of the amino acid.

3. The process as set forth in claim 1, wherein the molar ratio of the salt of the amino acid introduced into the salt compartment of the three-compartment bipolar membrane cell to the first acid of the aqueous electrolyte introduced into the acid compartment of the three-compartment bipolar membrane cell is from about 1:1 to about 1:10.

4. The process as set forth in claim 1, wherein the first acid is selected from the group consisting of HCl, $H_2SO_4$, $HNO_3$, $H_3PO_4$, HI, and combinations thereof.

5. The process as set forth in claim 1, wherein the temperature of the aqueous electrolyte is from about 10° C. to about 45° C. when introduced into the acid compartment.

6. The process as set forth in claim 1, wherein the first acid is introduced into the acid compartment of the three-compartment bipolar membrane cell gradually such that the pH within the acid compartment of the three-compartment bipolar membrane cell does not vary by more than about 1 pH unit per minute;
   wherein the pH of the contents of the acid compartment of the three-compartment bipolar membrane cell is less than about 3.0;
   wherein the concentration of salt of the amino acid in the feed salt stream is from about 5 wt % to about 30 wt %; and
   wherein the conductivity of the feed salt stream is between about 10 and about 250 mS/cm.

7. The process as set forth in claim 1, wherein the amino acid has the following structure:

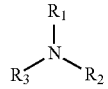

wherein $R_1$, $R_2$, and $R_3$ are independently selected from the group consisting of $CH_2C(O)OH$, $CH_2P(O)(OH)_2$, and hydrogen, wherein $R_1$, $R_2$, and $R_3$ are not each hydrogen.

8. The process of claim 7, wherein the amino acid is selected from the group consisting of iminodiacetic acid, N-(phosphonomethyl)iminodiacetic acid, glycine, and N-(phosphonomethyl)glycine and the salt of the amino acid comprises a cation selected from the group consisting of sodium, potassium, lithium, ammonium, calcium, and magnesium.

9. The process as set forth in claim 8, wherein the salt of the amino acid is disodium iminodiacetic acid and the amino acid is iminodiacetic acid.

10. The process as set forth in claim 1, further comprising one or more of:
    (i) recovering an acid product stream comprising the amino acid from the acid compartment of the three-compartment bipolar membrane cell;
    (ii) recovering a depleted salt stream from the salt compartment of the three-compartment bipolar membrane cell, the depleted salt stream comprising less than about 5 wt % of the salt of the amino acid; and
    (iii) recovering a base product stream from the base compartment of the three-compartment bipolar membrane cell.

11. The process as set forth in claim 10, wherein the acid product stream further comprises the salt of the amino acid from the acid compartment of the three-compartment bipolar membrane cell.

12. The process as set forth in claim 10, wherein the amino acid constitutes from about 2 to about 20 wt % of the acid product stream of the three-compartment bipolar membrane cell;
    wherein the amino acid content of the acid product stream of the three-compartment bipolar membrane cell represents a yield based on the amino acid salt introduced into the salt compartment of the three-compartment bipolar membrane cell of at least about 90%; and
    wherein the base content of the base product stream of the three-compartment bipolar membrane cell represents a yield based on the cation of the salt of the amino acid of at least about 90%.

13. The process as set forth in claim 1, wherein at least about 80% of the salt of the amino acid introduced into the salt compartment of the three-compartment bipolar membrane cell is converted to the amino acid recovered in the amino acid product stream.

14. The process as set forth in claim 1, wherein:
    the acid compartment of the three-compartment bipolar membrane cell is bounded by a first bipolar membrane and an anionic exchange membrane;
    the salt compartment of the three-compartment bipolar membrane cell is bounded by the anionic exchange membrane of the acid compartment and a cationic exchange membrane; and
    the base compartment bipolar membrane cell is bounded by a second bipolar membrane and the cationic exchange membrane.

15. The process as set forth in claim 14, wherein applying an electric potential between the cathode and the anode induces flow of protons in the acid compartment toward the cathode and formation of amino acid anions from the salt of the amino acid in the salt compartment, wherein the amino acid anions pass through the anionic exchange membrane and into the acid compartment.

16. The process as set forth in claim 15, wherein the three-compartment bipolar membrane cell further comprises one or more of:
  (i) an end membrane between the anode and a bipolar membrane, the end membrane selected from the group consisting of anion exchange membranes, cation exchange membranes, and bipolar membranes; and
  (ii) an end membrane between the cathode and a bipolar membrane, the end membrane selected from the group consisting of anion exchange membranes, cation exchange membranes, and bipolar membranes.

17. The process as set forth in claim 16, wherein the amino acid anions and the protons combine in the acid compartment of the three-compartment bipolar membrane cell to form the amino acid and cations from the salt of the amino acid and the hydroxide ions combine in the base compartment of the three-compartment bipolar membrane cell to form a base.

18. The process as set forth in claim 15, wherein applying an electric potential between the cathode and the anode comprises application of at least about 1 amperes (A) and application of at least about 5 volts (V).

19. The process of claim 1, wherein the current efficiency based on the transport of the cation of the salt of the amino acid to the base compartment of the three-compartment bipolar membrane cell is from about 85% to about 99%;
  wherein the current efficiency based on the transport of the anion of the salt of the amino acid to the acid compartment of the three-compartment bipolar membrane cell is from about 75% to about 99%; and
  wherein the specific power usage is less than about 1 kWhr/eq mol of the cation of the salt of the amino acid.

20. The process as set forth in claim 1, wherein the conductivity of the contents of the acid compartment of the three-compartment bipolar membrane cell is from about 20 mS/cm to about 300 mS/cm;
  wherein the conductivity of the contents of the salt compartment of the three-compartment bipolar membrane cell is less than about 200 mS/cm;
  wherein the conductivity of the contents of the base compartment of the three-compartment bipolar membrane cell is from about 10 mS/cm to about 500 mS/cm; and
  wherein the pH of the aqueous electrolyte within the acid compartment of the three-compartment bipolar membrane cell varies by less than about 1 pH unit per minute while the electric potential is applied between the cathode and the anode.

21. The process of claim 1, wherein the salt of the amino acid constitutes from about 10 wt % to about 20 wt % of the feed salt stream of the three-compartment bipolar membrane cell and the total power usage required to achieve a target yield of amino acid is less than about 5 kW/hr; wherein the target yield of amino acid is at least about 80%.

22. The process of claim 1, the process further comprising:
  introducing a feed salt stream comprising a salt of the amino acid into a salt compartment of a two-compartment electrodialysis bipolar membrane cell comprising the salt compartment and a base compartment;
  recovering a salt of the amino acid from the salt compartment of the two-compartment bipolar membrane cell, wherein at least a portion of the amino acid salt recovered from the salt compartment of the two-compartment bipolar membrane cell constitutes the feed salt stream introduced into the salt compartment of the three-compartment bipolar membrane cell; and
  recovering a base product from the base compartment of the two-compartment bipolar membrane cell;
  wherein the pH of the salt compartment of the three-compartment electrodialysis bipolar membrane cell is at least about 6, wherein the two-compartment bipolar membrane cell further comprises an anode and a cathode, the process further comprising:
  applying an electric potential between the cathode and the anode of the two compartment bipolar membrane cell.

23. The process of claim 22, wherein the salt compartment of the two-compartment bipolar membrane is bounded by a bipolar membrane and a cation exchange membrane and the base compartment of the two-compartment bipolar membrane is bounded by the cation exchange membrane bounding the salt compartment and a second bipolar membrane.

24. The process of claim 22, wherein applying an electric potential between the cathode and the anode of the two compartment bipolar membrane cell induces flow of cations from the salt of the amino acid in the salt compartment through the cation exchange membrane into the base compartment of the two-compartment bipolar membrane cell;
  wherein the current efficiency of the two-compartment bipolar membrane cell based on the transport of a cation of the salt of the amino acid to the base compartment is at least about 85%;
  wherein the power usage within the two-compartment bipolar membrane cell is less than about 5 kW/hr; and
  wherein the total combined power usage within the two-compartment bipolar membrane cell and the three-compartment bipolar membrane cell is less than about 10 kW/hr.

25. The process as set forth in claim 22, wherein the amino acid content of the acid product stream recovered from three-compartment bipolar membrane cell represents a yield based on the amino acid salt introduced into the salt compartment of two-compartment bipolar membrane cell of at least about 90%.

26. The process as set forth in claim 22, wherein the amino acid salt introduced into the salt compartment of the two-compartment bipolar membrane cell is disodium iminodiacetic acid; and wherein at least a portion of the amino acid salt recovered from the salt compartment of the two-compartment bipolar membrane cell that constitutes the feed salt stream introduced into the salt compartment of the three-compartment bipolar membrane cell is monosodium iminodiacetic acid.

27. A process for preparing an amino acid, the process comprising:
  introducing a feed salt stream comprising a salt of the amino acid into the salt compartment of a two-compartment electrodialysis bipolar membrane cell comprising a salt compartment and a base compartment;
  introducing the product from the salt compartment of the two-compartment electrodialysis bipolar membrane cell into the salt compartment of a three-compartment electrodialysis bipolar membrane cell comprising an acid compartment, a salt compartment, and a base compartment;
  introducing an aqueous electrolyte comprising a first acid into the acid compartment of the three-compartment electrodialysis bipolar membrane cell; and
  introducing an aqueous stream into the base compartment of the three-compartment electrodialysis bipolar membrane cell;
  wherein the first acid and the amino acid are different.

28. A process for preparing an amino acid, the process comprising:

introducing a feed salt stream comprising a salt of the amino acid into the salt compartment of a two-compartment electrodialysis bipolar membrane cell comprising a salt compartment, a base compartment, an anode and a cathode, wherein the salt compartment of the two-compartment bipolar membrane is bounded by a bipolar membrane and an cation exchange membrane and the base compartment of the two-compartment of the two-compartment bipolar membrane is bounded the cation exchange membrane bounding the salt compartment and second bipolar membrane;

applying an electric potential between the cathode and the anode of the two-compartment bipolar membrane cell, thereby inducing flow of cations from the salt of the amino acid in the salt compartment through the cation exchange membrane into the base compartment of the two-compartment bipolar membrane cell;

recovering a base product from the base compartment of the two-compartment bipolar membrane cell;

introducing the product from the salt compartment of the two-compartment electrodialysis bipolar membrane cell into the salt compartment of a three-compartment electrodialysis bipolar membrane cell comprising an acid compartment, a salt compartment, a base compartment, an anode and a cathode, introducing an aqueous electrolyte comprising a first acid into the acid compartment of the three-compartment electrodialysis bipolar membrane cell; and introducing an aqueous stream into the base compartment of the three-compartment electrodialysis bipolar membrane cell;

wherein the product from the salt compartment of the two-compartment bipolar membrane cell comprises an amino acid salt different from the amino acid salt introduced into the salt compartment of the two-compartment bipolar membrane cell.

29. The process of claim 27, wherein the first acid is hydrochloric acid and wherein the amino acid is iminodiacetic acid.

* * * * *